US009657081B2

(12) United States Patent
Gibot et al.

(10) Patent No.: US 9,657,081 B2
(45) Date of Patent: May 23, 2017

(54) INHIBITING PEPTIDES DERIVED FROM TRIGGERING RECEPTOR EXPRESSED ON MYELOID CELLS-1 (TREM-1) TREM-LIKE TRANSCRIPT 1 (TLT-1) FOR TREATMENT OF CARDIOVASCULAR DISEASES

(71) Applicants: INSERM (Institut National de la Sante et de la Recherche Medicale), Paris (FR); UNIVERSITE DE LORRAINE, Nancy (FR)

(72) Inventors: Sebastien Gibot, Nancy (FR); Amir Boufenzer, Nancy (FR); Hafid Ait-Oufella, Charenton-le-Pont (FR); Marc Derive, Chavigny (FR)

(73) Assignees: INSERM (INSTITUT NATIONAL DE LA SANTE ET DE LA RECHERCHE MEDICALE), Paris (FR); UNIVERSITE DE LORRAINE, Nancy (FR)

( * ) Notice: Subject to any disclaimer, the term of this patent is extended or adjusted under 35 U.S.C. 154(b) by 53 days.

(21) Appl. No.: 14/426,562

(22) PCT Filed: Sep. 9, 2013

(86) PCT No.: PCT/EP2013/068628
§ 371 (c)(1),
(2) Date: Mar. 6, 2015

(87) PCT Pub. No.: WO2014/037565
PCT Pub. Date: Mar. 13, 2014

(65) Prior Publication Data
US 2015/0232531 A1    Aug. 20, 2015

(51) Int. Cl.
*A61K 31/04* (2006.01)
*A61P 9/00* (2006.01)
*C07K 14/705* (2006.01)

(52) U.S. Cl.
CPC .............................. *C07K 14/70503* (2013.01)

(58) Field of Classification Search
None
See application file for complete search history.

(56) References Cited

U.S. PATENT DOCUMENTS

| 4,861,719 | A | 8/1989 | Miller |
| 5,278,056 | A | 1/1994 | Bank et al. |
| 5,882,887 | A | 3/1999 | Noeske-Jungblut et al. |
| 6,013,516 | A | 1/2000 | Verma et al. |
| 2004/0180409 | A1 | 9/2004 | McVicar et al. |
| 2008/0131423 | A1 | 6/2008 | Mori et al. |

FOREIGN PATENT DOCUMENTS

| WO | 9419478 | 9/1994 |
| WO | 9514785 | 6/1995 |
| WO | 9622378 | 7/1996 |
| WO | 2006056492 | 6/2006 |
| WO | 2009013319 | 1/2009 |
| WO | 2010124685 | 11/2010 |
| WO | 2011124685 | 10/2011 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Ait-Oufella et al "Recent advances on the role of cytokines in atherosclerosis" Arterioscler Thromb Vasc Biol. 2011, 31(5):969-979.
Binder and Lindblom "A Molecular View on the Interaction of the Trojan Peptide Penetratin with the Polar Interface of Lipid Bilayers" Biophys J, 2004, 87(1):332-343.
Bjorkbacka et al "Reduced atherosclerosis in MyD88-null mice links elevated serum cholesterol levels to activation of innate immunity signaling pathways" Nat Med. 2004, 10(4):416-421.
Chen et al "The role of triggering receptor expressed on myeloid cells-1 in the pathogenesis of acute viral myocarditis" Eur Heart J. 2010, 31(Supl 1):475-476.
Derive et al "Soluble TREM-like transcript-1 regulates leukocyte activation and controls microbial sepsis" J Immunol. 2012, 188(11):5585-92.
Derive et al "TREM-like transcript-1: At the frontier between haemostasis and inflammation" Hematologie. 2011, 17 (6):435-439.
Derive et al "Triggering receptor expressed on myeloid cells-1 as a new therapeutic target during inflammatory diseases" Self Nonself. 2010; 1(3):225-230.
Entman and Smith "Postreperfusion inflammation: A model for reaction to injury in cardiovascular disease" Cardiovasc Res. 1994, 28(9):1301-1311.
Gibot et al "Effects of the TREM-1 pathway modulation during mesenteric ischemia-reperfusion in rats" Crit Care Med. 2008; 36(2):504-510.
Gillies et al "A tissue-specific transcription enhancer element is located in the major intron of a rearranged immunoglobulin heavy chain gene" Cell. 1983, 33(3):717-728.
Hara and Saito "CARD9 versus CARMA1 in innate and adaptive immunity" Trends in Immunology. 2009, 30:234-242.

(Continued)

*Primary Examiner* — Christine J Saoud
*Assistant Examiner* — Jon M Lockard
(74) *Attorney, Agent, or Firm* — Whitham, Curtis & Cook, P.C.

(57) ABSTRACT

The present invention relates to a peptide comprising at least 6 consecutive amino acid selected from the amino acid sequence SEQ ID NO: 2 and a function-conservative variant. The invention also relates to a peptide comprising at least 6 consecutive amino acid selected from the amino acid sequence SEQ ID NO: 1 or SEQ ID NO: 2 and a function-conservative variant for use in the treatment of a cardiovascular disease.

6 Claims, 28 Drawing Sheets

(56) References Cited

OTHER PUBLICATIONS

Hartwell et al "Role of P-selectin cytoplasmic domain in granular targeting in vivo and in early inflammatory responses" Journal of Cell Biology. 1998, 143(4):1129-1141.
Kuwana et al "Production of the constant domain of murine T-cell receptor beta-chain in *Escherichia coli*" FEBS Letter. 1987, 219(2):360-364.
Libby "Inflammation in atherosclerosis" Nature. 2002, 420(6917):868-874.
Mason et al "Transcription cell type specificity is conferred by an immunoglobulin VH gene promoter that includes a functional consensus sequence" Cell. 1985, 41(2):479-487.
Mehta and Li "Inflammation in ischemic heart disease: response to tissue injury or a pathogenetic villain" Cardiovasc Res. 1999, 43(2):291-299.
Mizukami and Itoh "A new SV40-based vector developed for cDNA expression in animal cells" J Biochem. 1987, 101(5):1307-1310.
Nahrendorf et al "The healing myocardium sequentially mobilizes two monocyte subsets with divergent and complementary functions" J Exp Med. 2007, 204(12):3037-3047.
Potteaux et al "Suppressed monocyte recruitment drives macrophage removal from atherosclerotic plaques of Apoe-/- mice during disease regression" J Clin Invest. 2011, 121(5):2025-2036.
Radsak et al "Triggering receptor expressed on myeloid cells-1 in neutrophil inflammatory responses: differential regulation of activation and survival" J. Immunol. 2004, 172:4956-4963.
Saini et al "Role of tumour necrosis factor-alpha and other cytokines in ischemia-reperfusion-induced injury in the heart" Exp Clin Cardiol. 2005, 10(4):213-222.
Swirski et al "Identification of splenic reservoir monocytes and their deployment to inflammatory sites" Science. 2009, 325(5940):612-616.
Wang et al "TREM-A is a positive regulator of TNF-(alpha) and IL-8 production in U937 foam cells" Bosnian journal of basic medical sciences. 2012, 12(2):94-101.
Washington et al "A TREM family member, TLT-1, is found exclusively in the alpha-granules of megakaryocytes and platelets" Bood. 2004, 104(4):1042-1047.
Washington et al "TREM-like transcript-1 protects against inflammation-associated hemorrhage by facilitating platelet aggregation in mice and humans" J Clin Invest 2009, 119(6)1489-501.
International Search Report of PCT/EP2013/068628 (WO2014/037565).

* cited by examiner

A

B

B

C

INHIBITING PEPTIDES DERIVED FROM TRIGGERING RECEPTOR EXPRESSED ON MYELOID CELLS-1 (TREM-1) TREM-LIKE TRANSCRIPT 1 (TLT-1) FOR TREATMENT OF CARDIOVASCULAR DISEASES

FIELD OF INVENTION

The invention relates to a peptide comprising at least 6 consecutive amino acid selected from the amino acid sequence SEQ ID NO: 2 and a function-conservative variant. The invention also relates to a peptide comprising at least 6 consecutive amino acid selected from the amino acid sequence SEQ ID NO: 1 or SEQ ID NO: 2 and a function-conservative variant for use in the treatment of a cardiovascular disease.

BACKGROUND OF INVENTION

Cardiovascular disease, the hallmark of many diseases, is a leading process of death worldwide.

Myocardial or cerebral infarction exemplifies a complex clinical syndrome that results from a harmful and damaging, permanent or transitional, myocardial ischemia. This is usually caused by coronary/cerebral artery occlusion, resulting in an imbalance between oxygen supply and demand.

Tissue damages depend on the duration of ischemia. For ischemia as short as 5 minutes, the ischemic tissue ultimately recovers after reperfusion, without infarction symptoms or lethal consequences. However, ischemia of significant duration leads to infarction and inflammatory reaction. Indeed, infarction is associated with an inflammatory reaction, which is a prerequisite of healing and scar formation [Entman M. L. et al., 1994 and Mehta J. L. et al., 1999]. This response is amplified in terms of magnitude and duration when the ischemic tissue is reperfused.

This response is multiphasic: initial ischemia induces necrosis, formation of free radical oxygen species, complement activation, and a cytokine cascade initiated by TNF-alpha release. Reperfusion phase of the infracted area is associated with an increased and accelerated inflammatory reaction responsible for leucocytes recruitment at the site of ischemia. Recruited leucocytes also participate to an in situ and systemic release of inflammatory mediators, leading in fine to a hyperactivated inflammatory state, responsible for pathophysiological consequences of infarction.

All the inflammatory mediators have controversial effects. Indeed, infarction physiopathology is balanced between their beneficial and adverse effects. For example, TNF-alpha displays cytoprotective effects during myocardial ischemia, as well as deleterious effects [Harjot K Saini. et al., 2005], depending on time, duration and level of its expression and release. This may explain the complexity of a therapy based on blocking such inflammatory mediators.

Release of mediators of inflammation (cytokines, chemokines, ROS . . . ) and massive leukocyte recruitment play an important role during all stages of the ischemic cascade, from the early damaging events triggered by arterial occlusion to the late regenerative processes underlying post-ischemic tissue-repair. Many therapeutic strategies targeting this inflammatory response failed to demonstrate any efficacy. It seems now obvious that it is worth tempting to act on amplification loops rather than on individual ischemia-induced inflammatory mediator.

Atherosclerosis gives rise to cerebrovascular disease and coronary artery disease through a slowly progressing lesion formation and luminal narrowing of arteries. Upon plaque rupture and thrombosis, these most common forms of cardiovascular disease manifest as acute coronary syndrome (ACS), myocardial infarction or stroke. Human and animal studies have established that atherosclerosis is driven by a chronic inflammatory process within the arterial wall initiated mainly in response to endogenously modified structures, particularly oxidized lipoproteins that stimulate both innate and adaptive immune responses. The innate response is instigated by the activation of both vascular cells and monocytes/macrophages, subsequently an adaptive immune response develops against an array of potential antigens presented to effector T lymphocytes by antigen-presenting cells [Ait-Oufella H et al., 2011]. Genetically modified mouse models taught us that circulating monocytes were recruited into the vascular wall by chemokines and then become macrophages and lipid-loaded foam cells. Intima macrophages promote plaque development through cytokine release, inflammation amplification and plaque destabilization through protease production and apoptosis accumulation [Libby P. 2002].

Monocytes/macrophages are stimulated by several mediators named PAMPs (for Pathogen Associated Molecular Patterns) that interact with PRRs (for Pathogen Recognition Receptors). Several PRRs are implicated in the physiopathology in atherosclerosis. For example, Toll-like receptors are expressed in human and animal atherosclerotic lesions. TLR inhibition reduces atherosclerosis development in mice suggesting that targeting such pathways could be atheroprotective [Bjorkbacka H et al., 2004].

Recently, a new family of receptors expressed on myeloid cells has been described: Triggering Receptors Expressed on Myeloid cells (TREMs). Among this family, TREM-1 is expressed on monocytes/macrophages and neutrophils. TREM-1 activation leads to cytokines and chemokines production (TNF-α, IL-6, IL-8, MCP-1 and -3, MIP-1α . . . ) along with rapid neutrophil degranulation and oxidative burst [Radsak M P et al., 2004 and Hara H, et al., 2009].

The TREM-1 function is to modulate/amplify rather than to activate/initiate inflammation by synergizing with TLRs in order to trigger an exuberant immune response. Pathophysiological role of TREM-1 was firstly identified during infectious diseases. TREM-1 is known to play a crucial role during aseptic inflammation, both acute (mesenteric ischemia-reperfusion, hemorrhagic choc, pancreatitis . . . ) and chronic (Inflammatory Bowel Diseases, Rheumatic diseases . . . ).

TLT-1 (Trem-Like Transcript-1) is a member of TREM family but exclusively found in megakaryocytes and platelets. TLT-1 was first identified to play a role during platelet aggregation by linking fibrinogen and stabilizing platelet aggregate. But new findings from the inventor's laboratory on TLT-1, soluble TLT-1 and sTLT-1-derived polypeptides have shown that TLT-1 plays a role during inflammation by specifically inhibiting TREM-1 [Derive M et al., 2012, WO2010/124685].

Washington et al. described that TLT-1 plays a protective role during inflammation by facilitating platelet aggregation at sites of vascular injury (Washington et al. J Clin Invest. 2009).

Since it is known that platelet aggregation is associated with a worst outcome during cardiovascular diseases (e.g. myocardial infarction and atherosclerosis), it was surprising to find that TLT-1-derived peptides have a therapeutic effect on cardiovascular diseases.

The inventors herein describe that TREM-1 is expressed 1) by the endothelial cells from aorta, mesenteric artery, and microvascular cells 2) by myocardial tissue and that its expression is up-regulated in infarcted areas following myocardial ischemia (permanent myocardial ischemia and transient myocardial ischemia) 3) by the macrophages recruited into atheromatous plaques.

They also show that both TREM-1 and TLT-1-derived peptides are able to specifically inhibit TREM-1, and decrease TREM-1 associated inflammatory response in myocardial infarction, and atherosclerosis.

As a result, administration of these peptides during acute phase of 2 different models of myocardial ischemia (permanent ischemia and transient ischemia) was responsible for a modulation of in situ inflammatory response and ensuing leucocyte trafficking, thus limiting post-ischemic cardiac remodelling and later stages of disease progression. Indeed, cardiac function was dramatically improved 6 weeks after permanent ischemia as well as transient ischemia (ischemia-reperfusion) event. This translated into survival gain.

They finally demonstrate a role of TREM-1 and TLT-1-derived peptides in reducing the extend of atheromatous plaque formation by specifically inhibiting TREM-1.

Thus, the invention relates to a peptide comprising at least 6 consecutive amino acid selected from the amino acid sequence SEQ ID NO: 2 and a function-conservative variant.

Moreover, the invention relates to a peptide comprising at least 6 consecutive amino acid selected from the amino acid sequence SEQ ID NO: 1 or SEQ ID NO: 2 and a function-conservative variant or an isolated nucleic acid, an expression vector, a host cell according to the invention for use in the treatment of a cardiovascular disease.

SUMMARY

One object of the invention is a peptide comprising at least 6 consecutive amino acids selected from the amino acid sequence SEQ ID NO: 1 or SEQ ID NO: 2 and a function-conservative variant for use in the treatment of a cardiovascular disease.

In one embodiment, said peptide comprises a 6 consecutive amino acid sequence selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12 for use in the treatment of a cardiovascular disease.

In one embodiment, the cardiovascular disease is a myocardial infarction.

In another embodiment, the cardiovascular disease is atherosclerosis.

Another object of the invention is a peptide comprising at least 6 consecutive amino acids selected from the amino acid sequence SEQ ID NO: 2 and a function-conservative variant.

In one embodiment, said peptide comprises a 6 consecutive amino acid sequence selected from the group consisting of SEQ ID NO: 10, SEQ ID NO: 11 or SEQ ID NO: 12.

In another embodiment, said peptide comprises an amino acid sequence as set forth in SEQ ID NO: 8 or SEQ ID NO: 9.

In another embodiment, said peptide consists of an amino acid sequence as set forth in SEQ ID NO: 8, SEQ ID NO: 9, SEQ ID NO: 10, SEQ ID NO: 11 or SEQ ID NO: 12.

Another object of the invention is an isolated nucleic acid sequence coding for a peptide as described here above.

Another object of the invention is an expression vector containing a nucleic acid sequence as described here above.

Another object of the invention is a host cell comprising an expression vector as described here above.

Another object of the invention is a pharmaceutical composition comprising a therapeutically effective amount of at least one peptide as described here above, or a nucleic acid as described here above, or an expression vector as described here above or a host cell as described here above along with at least one pharmaceutically acceptable excipient.

DETAILED DESCRIPTION

Definitions

Throughout the specification, several terms are employed and are defined in the following paragraphs.

As used herein, the term "TLT-1" for "TREM-like transcript 1" denotes a member of the TREM family. The initial work from McVicar group [Washington A. V. et al., 2004] demonstrated that TLT-1 is abundant, specific to the platelet and megakaryocyte lineage, and is sequestered in the platelet a granules. Upon platelet activation with thrombin or LPS, TLT-1 is translocated to the platelet surface. TLT-1 contains a v-set Ig type-extracellular domain, a transmembrane region and a cytoplasmic tail that comprises an immunoreceptor tyrosine-based inhibitory motif (ITIM) and a polyproline-rich domain. Unlike other TREM family members, TLT-1 does not couple to the DAP 12 activating chain whereas it has been shown to enhance $Ca^{++}$ signalling in rat basophilic leukemia (RBL) cells, suggesting TLT-1 is a co-activating receptor. The amino acid sequence of TLT-1 is described as the amino acid sequence SEQ ID NO: 1.

As used herein, the term "TREM-1" for "Triggering receptor expressed on myeloid cells 1" denotes a cell-surface molecule that has been identified both on human and murine polymorphonuclear neutrophils and mature monocytes. It belongs to the immunoglobulin superfamily and activates downstream signalling pathways with the help of an adapter protein called DAP12. The expression of TREM-1 is greatly up-regulated on neutrophils and monocytes in the presence of such bacteria as *Pseudomonas aeruginosa* or *Staphylococcus aureus*, both in cell culture and in tissue samples from patients with infection. In striking contrast, TREM-1 is not up-regulated in samples from patients with non-infectious inflammatory diseases such as psoriasis, ulcerative colitis or vasculitis caused by immune complexes. Moreover, when TREM-1 is bound to its ligand, a synergistic effect of LPS and an amplified synthesis of the pro-inflammatory cytokines such as TNF-[alpha] are observed together with an inhibition of IL-10 production. The amino acid sequence of TREM-1 is described as the amino acid sequence SEQ ID NO: 2.

Peptides of the invention, also called TREM-1- and TLT-1-derived peptides, are described in the table 1 below.

TABLE 1 peptides of the inventions.

| Peptide name | Sequence | SEQ ID |
|---|---|---|
| TLT1-LR17 | LQEEDAGEYGCMVDGAR | SEQ ID NO: 3 |
| TLT1-LR12 | LQEEDAGEYGCM | SEQ ID NO: 4 |
| TLT1-LR6-1 | LQEEDA | SEQ ID NO: 5 |
| TLT1-LR6-2 | EDAGEY | SEQ ID NO: 6 |
| TLT-1-LR6-3 | GEYGCM | SEQ ID NO: 7 |
| TREM1-LP17 | LQVEDSGLYQCVIYQPP | SEQ ID NO: 8 |

TABLE 1-continued peptides of the inventions.

| Peptide name | Sequence | SEQ ID |
|---|---|---|
| TREM1-LP12 | LQVEDSGLYQCV | SEQ ID NO: 9 |
| TREM1-LP6-1 | LQVEDS | SEQ ID NO: 10 |
| TREM1-LP6-2 | EDSGLY | SEQ ID NO: 11 |
| TREM1-LP6-3 | GLYQCV | SEQ ID NO: 12 |
| TLT-1 LR12 scramble | ELMEGGQECADY | SEQ ID NO: 13 |

As used herein, the term "Function-conservative variants" denotes peptides derived from a peptide of the invention in which a given amino acid residue in a protein or enzyme has been changed without altering the overall conformation and function of the peptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent of protein or amino acid sequence similarity between any two proteins of similar function may vary and may be, for example, from 70% to 99% as determined according to an alignment method such as by the Cluster Method, wherein similarity is based on the MEGALIGN algorithm. A "function-conservative variant" also includes a peptide which has at least 20% amino acid identity as determined by BLAST or FASTA algorithms, preferably 40% more preferably 60%, preferably at least 75%, most preferably at least 85%, and even more preferably at least 90%, and which has the same or substantially similar properties or functions as the native or parent protein to which it is compared.

As used herein, the term "derivative" refers to a variation of a peptide of the invention or of a function-conservative variant thereof that are otherwise modified, i.e. by covalent attachment of any type of molecule to the peptide, by addition of chemical compound in any of the amino-acids of the sequence, in order to modify in vitro or in vivo conformation, activity, specificity, efficacy or stability of the peptide.

As used herein, the terms "treating" or "treatment", denotes reversing, alleviating, inhibiting the progress of, or preventing the disorder or condition to which such term applies, or one or more symptoms of such a disorder or condition.

According to the invention the terms "pharmaceutically" or "pharmaceutically acceptable" denotes entities and compositions that do not produce an adverse, allergic or other non desired reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

According to the invention, the term "patient" or "individual" to be treated is intended for a human or non-human mammal (such as a rodent (mouse, rat), a feline, a canine, or a primate) affected or likely to be affected by inflammatory disorders. Preferably, the subject is a human.

Peptides of the Invention

A first aspect of the invention relates to a peptide comprising at least 6 consecutive amino acid selected from the amino acid sequence SEQ ID NO: 2 and a function-conservative variant.

Another aspect of the invention relates to a peptide comprising at least 6 consecutive amino acid selected from the amino acid sequence SEQ ID NO: 1 and a function-conservative variant.

In one embodiment, said peptide is not SEQ ID NO: 1.
In one embodiment, said peptide is not SEQ ID NO: 2.
In one embodiment, the peptide has a length of less than 50 amino acids, less than 40, 35, 30, 25, 20 amino acids.

In a preferred embodiment, the peptide according to the invention has a length of 6 to 20 amino acids, or 10 to 20 amino acids, or 12 to 18 amino acids or 14 to 16 amino acids.

In a preferred embodiment, the peptide according to the invention has a length of 3, 4, 5, 6, 7, 8, 9, 10, 11, 12, 13, 14, 15, 16, 17, 18, 19 or 20 amino acids.

In another embodiment, the peptide according to the invention comprises a 6 consecutive amino acid sequence selected from the group consisting of SEQ ID NO: 5, SEQ ID NO: 6, SEQ ID NO: 7, SEQ ID NO: 10, SEQ ID NO: 11 or SEQ ID NO: 12.

In another preferred embodiment, the peptide according to the invention comprises an amino acid sequence as set forth in SEQ ID NO: 3 or SEQ ID NO: 8.

In another preferred embodiment, the peptide according to the invention comprises an amino acid sequence as set forth in SEQ ID NO: 4 or SEQ ID NO: 9.

In another preferred embodiment, the peptide according to the invention consists of an amino acid sequence as set forth in SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12.

In another embodiment, the peptide according to the invention may have D- or L-configuration.

In another embodiment, the amino acid from the amino end of the peptide according to the invention has an acetylated terminal amino group, and the amino acid from the carboxyl end has an amidated terminal carboxy group. Therefore, the invention also includes derivatives of the peptide of the invention in which the amino-terminal end is acetylated or in which where the carboxy-terminal end is amidated.

In addition, peptides according to the invention may undergo reversible chemical modifications in order to increase its bioavailability (including stability and fat solubility) and its ability to pass the blood-brain barrier and epithelial tissue. Examples of such reversible chemical modifications include esterification of the carboxy groups of glutamic and aspartic amino acids with an alcohol, thereby removing the negative charge of the amino acid and increasing its hydrophobicity. This Esterification is reversible, as the ester link formed is recognized by intracellular esterases which hydrolyze it, restoring the charge to the aspartic and glutamic residues. The net effect is an accumulation of intracellular peptide, as the internalized, de-esterified peptide cannot cross the cell membrane.

Another example of such reversible chemical modifications include the addition of a further peptidic sequence, which allows the increase of the membrane permeability, such as a TAT peptide or Penetratin peptide (see—Charge-Dependent Translocation of the Trojan. A Molecular View on the Interaction of the Trojan Peptide Penetratin with the Polar Interface of Lipid Bilayers. Biophysical Journal, Volume 87, Issue 1, 1 Jul. 2004, Pages 332-343).

Peptides according to the invention may be obtained through conventional methods of solid-phase chemical peptide synthesis, following Fmoc and/or Boc-based 20 methodology (see Pennington, M. W. and Dunn, B. N. (1994). Peptide synthesis protocols. Humana Press, Totowa.).

Alternatively, peptides according to the invention may be obtained through conventional methods based on recombinant DNA technology, e.g., through a method that, in brief, includes inserting the nucleic acid sequence coding for the peptide of the invention into an appropriate plasmid or vector, transforming competent cells for said plasmid or vector, and growing said cells under conditions that allow the expression of the peptide of the invention and, if desired, isolating and (optionally) purifying the peptide of the invention through conventional means known to experts in these matters. The nucleic acid sequence that codes for the peptide of the invention may be easily deduced from the correspondence that exists between the amino acids and the nucleotide codons that code for such amino acids. In this case, an additional object of the invention is an isolated nucleic acid sequence that codes for the peptide of the invention. In one particular embodiment, said nucleic acid is selected from single-strand DNA, double-stranded DNA, and RNA. Additional objects of this invention are plasmids and expression vectors that contain said nucleic acid sequence that codes for the peptide of the invention, as well as prokaryotic or eukaryotic cells that express the peptide of the invention. A review of the principles of recombinant DNA technology may be found, for example, in the text book entitled "Principles of Gene Manipulation: An Introduction to Genetic Engineering," R. W. Old & S. B. Primrose, published by Blackwell Scientific Publications, 4th Edition (1989).

As described, the invention also includes peptides which are functionally equivalent to the peptides of the invention or "function-conservative variant". In the sense used in this description, the expression "functionally equivalent" means that the peptide in question has at least one of the biological activities of the peptide of the invention, such as, for example, the ability to decrease the inflammation.

The effect of the peptides of the invention will become evident to the skilled person by implementing a simple test to evaluate the decrease of inflammation in cardiovascular diseases due to the peptides. For example, $5 \times 10^5$ isolated human neutrophils or macrophages or endothelial cells are incubated in presence of 100 ng/mL LPS and/or 10 µg/mL anti-TREM-1 mAb with or without 20 µg/mL of polypeptide for 24 hours at 37° C./5% $CO_2$. Supernatant is then collected and TNF-α, IL-6 and GM-CSF concentrations measured by ELISA. If the studied peptide inhibits TREM-1, cytokine concentrations must decrease by up to 30% or more as compared to conditions without peptide.

Nucleic Acids, Vectors and Recombinant Host Cells of the Invention

A second aspect of the invention relates to a nucleic acid molecule encoding peptides according to the invention.

In a preferred embodiment, the nucleic acid molecule encoding for a peptide which has a sequence SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12.

A "coding sequence" or a sequence "encoding" an expression product, such as a RNA, peptide, protein, or enzyme, is a nucleotide sequence that, when expressed, results in the production of that RNA, peptide, protein, or enzyme, i.e., the nucleotide sequence encodes an amino acid sequence for that peptide, protein or enzyme. A coding sequence for a protein may include a start codon (usually ATG) and a stop codon.

These nucleic acid molecules may be obtained by conventional methods well known to those skilled in the art, in particular by site-directed mutagenesis of the gene encoding the native protein. Typically, said nucleic acid is a DNA or RNA molecule, which may be included in a suitable vector, such as a plasmid, cosmid, episome, artificial chromosome, phage or viral vector.

So, a further object of the present invention relates to a vector and an expression cassette in which a nucleic acid molecule of the invention is associated with suitable elements for controlling transcription (in particular promoter, enhancer and, optionally, terminator) and, optionally translation, and also the recombinant vectors into which a nucleic acid molecule in accordance with the invention is inserted. These recombinant vectors may, for example, be cloning vectors, or expression vectors.

The terms "vector", "cloning vector" and "expression vector" mean the vehicle by which a DNA or RNA sequence (e.g. a foreign gene) may be introduced into a host cell, so as to transform the host and promote expression (e.g. transcription and translation) of the introduced sequence.

Any expression vector for animal cell may be used, as long as a gene encoding a peptide or chimeric derivative of the invention can be inserted and expressed. Examples of suitable vectors include pAGE107, pAGE103, pHSG274, pKCR, pSG1 beta d2-4 and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

The invention also includes gene delivery systems comprising a nucleic acid molecule of the invention, which can be used in gene therapy in vivo or ex vivo. This includes for instance viral transfer vectors such as those derived from retrovirus, adenovirus, adeno associated virus, lentivirus, which are conventionally used in gene therapy. This also includes gene delivery systems comprising a nucleic acid molecule of the invention and a non-viral gene delivery vehicle. Examples of non viral gene delivery vehicles include liposomes and polymers such as polyethylenimines, cyclodextrins, histidine/lysine (HK) polymers, etc.

Another object of the invention is also a prokaryotic or eukaryotic host cell genetically transformed with at least one nucleic acid molecule according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

Preferably, for expressing and producing the peptides, and in particular the peptide according to the invention, eukaryotic cells, in particular mammalian cells, and more particularly human cells, will be chosen.

Typically, cell lines such as CHO, BHK-21, COS-7, C127, PER.C6 or HEK293 could be used, for their ability to process to the right post-translational modifications of the derivatives.

The construction of expression vectors in accordance with the invention, the transformation of the host cells can be carried out using conventional molecular biology techniques. The V-ATPase c-subunit derivatives of the invention, can, for example, be obtained by culturing genetically transformed cells in accordance with the invention and recovering the derivative expressed by said cell, from the culture. They may then, if necessary, be purified by conventional procedures, known in themselves to those skilled in the art, for example by fractionated precipitation, in particular ammonium sulphate precipitation, electrophoresis, gel filtration, affinity chromatography, etc.

In particular, conventional methods for preparing and purifying recombinant proteins may be used for producing the proteins in accordance with the invention.

Therapeutic Methods, Uses and Pharmaceutical Compositions

A third object of the present invention relates to a peptide according to the invention for use in the treatment of a cardiovascular disease.

An object of the invention is a method for treating a cardiovascular disease in a subject in need thereof, comprising administering to the subject a therapeutically effective amount of a peptide as described here above. In one embodiment, said method comprises administering a peptide as described here above, wherein said peptide inhibits TREM-1.

Cardiovascular disease according to the invention including but are not limited to myocardial and cerebral infarction, acute myocardial infarction, ischemia, coronary heart disease, acute coronary syndrome, stroke, aneurysm, stable or effort angina pectoris, cardiomyopathy, hypertensive heart disease, heart failure (chronic and acute), cor pulmonale, cardiac dysrhythmias, inflammatory heart disease such as endocarditis, myocarditis, peripheral arterial disease, SIRS-associated myocardial and vascular dysfunction, atherosclerosis.

In one embodiment, the cardiovascular disease condition is myocardial infarction.

In another embodiment, the cardiovascular disease condition is atherosclerosis.

In another embodiment, the cardiovascular disease condition is SIRS-associated myocardial and vascular dysfunction.

In one embodiment, the cardiovascular disease is not mesenteric ischemia reperfusion.

In another embodiment, the cardiovascular disease does not comprise cardiovascular protection during polymicrobial sepsis.

In one embodiment, the peptides of the invention are not used for treating sepsis.

In one embodiment, the peptides of the invention are not used for treating ischemia and reperfusion syndromes.

In one embodiment, the peptides of the invention are not used for treating patients with hypercoagulatory conditions.

In one embodiment, the peptides of the invention are not used for treating inflammation-associated haemorrhage.

In one embodiment, the peptides of the invention are not used for treating acute viral myocarditis.

In one embodiment of the invention, the peptides of the invention are used for treating a cardiovascular disease selected in the group consisting of myocardial and cerebral infarction, myocardic ischemia, coronary heart disease, stroke, aneurysm, stable or effort angina pectoris, cardiomyopathy, hypertensive heart disease, heart failure (chronic and acute), cor pulmonale, cardiac dysrhythmias, inflammatory heart disease such as endocarditis, myocarditis, peripheral arterial disease, SIRS-associated myocardial and vascular dysfunction, and atherosclerosis.

A particular embodiment, the invention relates to a peptide comprising at least 6 consecutive amino acid selected from the amino acid sequence SEQ ID NO 2 and a function-conservative variant or to a peptide comprising at least 6 consecutive amino acid selected from the amino acid sequence SEQ ID NO 1 and a function-conservative variant for use in the treatment of a cardiovascular disease.

In a particular embodiment, the invention relates to a peptide of an amino acid sequence as set forth in SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12 for use in the treatment of a cardiovascular disease.

In one embodiment, the invention also relates to an isolated nucleic acid according to the invention or to a plasmid according to the invention or to an expression vector according to the invention or to a host cell according to the invention for use in the treatment of a cardiovascular disease.

Peptides according to the invention are able to treat inflammatory condition through its properties of decoy receptor.

By "decoy receptor", is meant that polypeptides according to the invention (TREM-1 and TLT-1-derived peptides) trap the TREM-1 ligand and prevent its physiological effects on TREM-1.

Peptides according to the invention could therefore form part of a combined therapy (aimed at several therapeutic targets) with the objective of more effectively stopping cardiovascular disease.

An additional object of this invention is a pharmaceutical composition which includes a therapeutically effective amount of at least one peptide according to the invention, along with at least one pharmaceutically acceptable excipient. In one particular embodiment, said pharmaceutical composition also contains one or more (COOH) peptides. Alternatively, the pharmaceutical composition of the invention may contain a therapeutically effective amount of a vector that contains at least one nucleic acid sequence that codes for a peptide of the invention, along with at least one adjuvant and/or a pharmaceutically acceptable excipient. Said vector may be used in gene therapy.

By a "therapeutically effective amount" is meant a sufficient amount of the chimeric derivative of the invention to treat cardiovascular disease at a reasonable benefit/risk ratio applicable to any medical treatment.

It will be understood that the total daily dosage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific peptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The active products of the invention (peptides, nucleic acid, plasmid, expression vector or host cell) may be administered for use in the treatment of cardiovascular diseases. The therapeutically effective amount of the active product of the invention [peptides or vectors (constructions)] that should be administered, as well as the dosage for the treatment of a pathological condition with the peptides and/or pharmaceutical compositions of the invention, will depend on numerous factors, including the age and condition of the patient, the severity of the disturbance or disorder, the method and frequency of administration and the particular peptide to be used.

The presentation of the pharmaceutical compositions that contain the peptides or vectors (constructions) of the invention may be in any form that is suitable for administration, e.g., solid, liquid or semi-solid, such as creams, ointments, gels or solutions, and these compositions may be administered by any suitable means, for example, orally, parenterally, inhalation or topically, so they will include the pharmaceutically acceptable excipients necessary to make up the desired form of administration. A review of the different pharmaceutical forms for administering medicines and of the excipients necessary for obtaining same may be found, for example, in the "Tratado de Farmacia Gal nica" (Treatise on Galenic Pharmacy), C. Faul i Trillo, 1993, Luz n 5, S.A. Ediciones, Madrid.

In the pharmaceutical compositions of the present invention for oral, sublingual, subcutaneous, intramuscular, intravenous, transdermal, local, pulmonary or rectal administration, the active principle, alone or in combination with another active principle, can be administered in a unit administration form, as a mixture with conventional pharmaceutical supports, to animals and human beings. Suitable unit administration forms comprise oral route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, allow the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Peptides according to the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active peptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variations in dosage will necessarily occur depending on the conditions of the subject being treated. The person responsible for administration will, in any event, determine the appropriate dose for the individual subject.

The peptide of the invention may be formulated as a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

As previously mentioned, the peptides according to the invention could form part of a combined therapy for the purpose of more effectively stopping cardiovascular disease. In this case, the invention provides a pharmaceutical composition that includes at least one peptide of the invention; along with another or other anti-cardiovascular disease compound(s) for example statin compounds, anticoagulant approaches, anti-aldosterone compounds, ACE inhibitors (Angiotensin converting enzyme inhibitor) and Beta-blockers.

In addition, the invention provides a method for the treatment of a cardiovascular disease in mammals which consists of administering to said mammal suffering from said cardiovascular disease a therapeutically effective amount of at least one peptide of the invention, or of a vector containing at least one DNA sequence that codes for a peptide of the invention, preferably in the form of a pharmaceutical composition that contains it. In one particular embodiment of this invention, said pharmaceutical composition contains, in addition to the peptide or peptides of the invention, one or more (COOH) peptides.

In one embodiment, cardiovascular disease according to the invention including but are not limited to myocardial and cerebral infarction, acute myocardial infarction, ischemia, coronary heart disease, acute coronary syndrome, stroke, aneurysm, stable or effort angina pectoris, cardiomyopathy, hypertensive heart disease, heart failure (chronic and acute), cor pulmonale, cardiac dysrhythmias, inflammatory heart disease such as endocarditis, myocarditis, peripheral arterial disease, SIRS-associated myocardial and vascular dysfunction, atherosclerosis.

The invention will be further illustrated by the following figures and examples. However, these examples and figures should not be interpreted in any way as limiting the scope of the present invention.

Concentration-response curves to phenylephrine (A and B) and acetylcholine (C) in aortic rings. Aortas were harvested from healthy rats and stimulated in vitro with αTREM-1 (5 µg/mL) and LPS (10 µg/mL) with or without TREM-1- and TLT-1-derived peptides or LR12-scrambled peptide. B: some aortas were desendothelialized (-E). Data are representative of at least 5 different experiments, p values: *p<0.05, p<0.01, *p<0.001, ns: non-significant.

Figure 2:
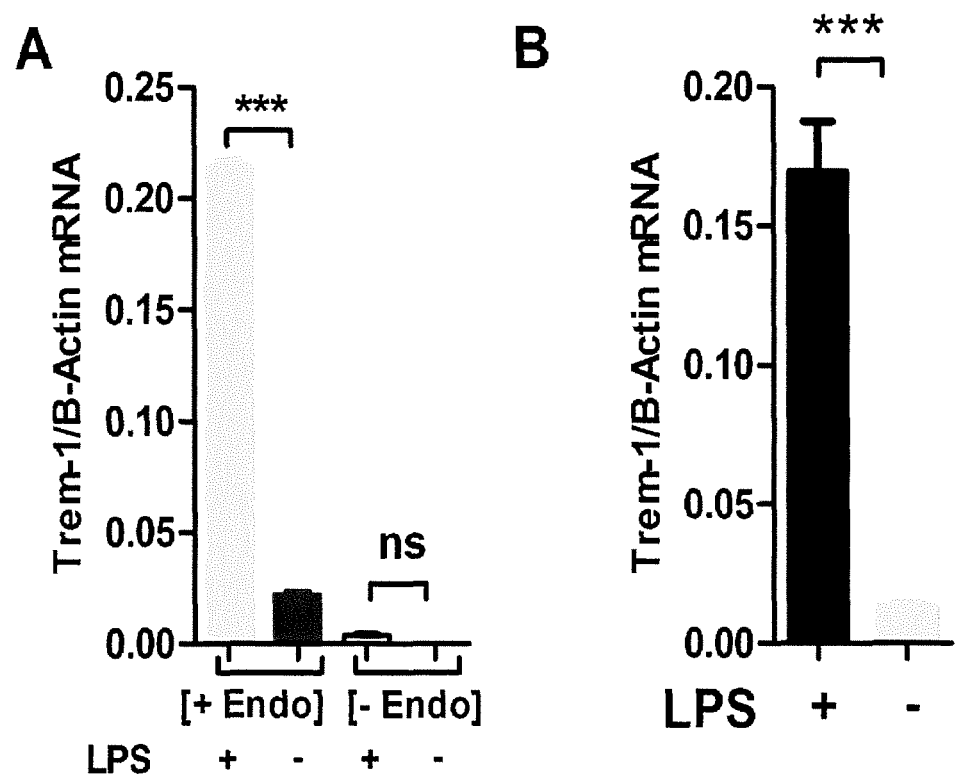

FIG. 2: TREM-1 is expressed in endothelial cells from conductives and resistives arteries.

Mouse aorta (a conductive artery) (A) and rat mesenteric artery (a resistive artery) (B) were stimulated with or without LPS as indicated. Trem-1 expression was determined by qRT-PCR. Data are representative of at least 5 different experiments, p values: ***p value <0.001. ns (not significant).

Figure 3:
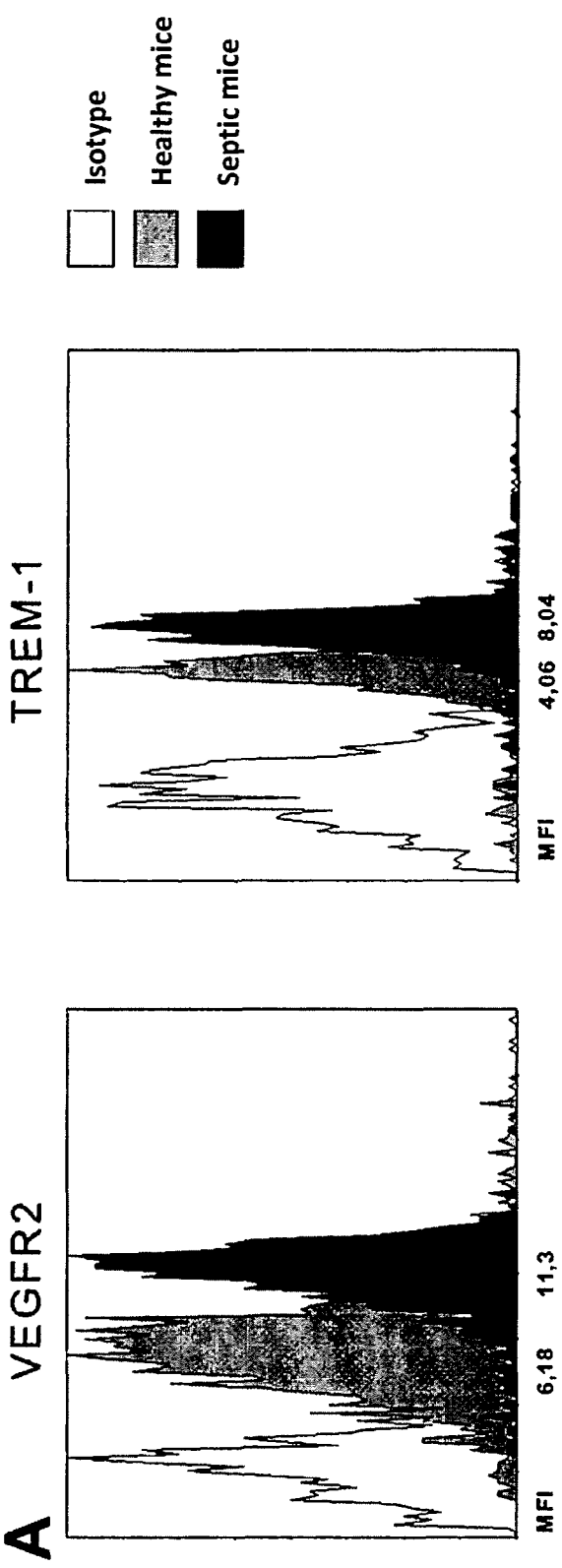
Figure 3:
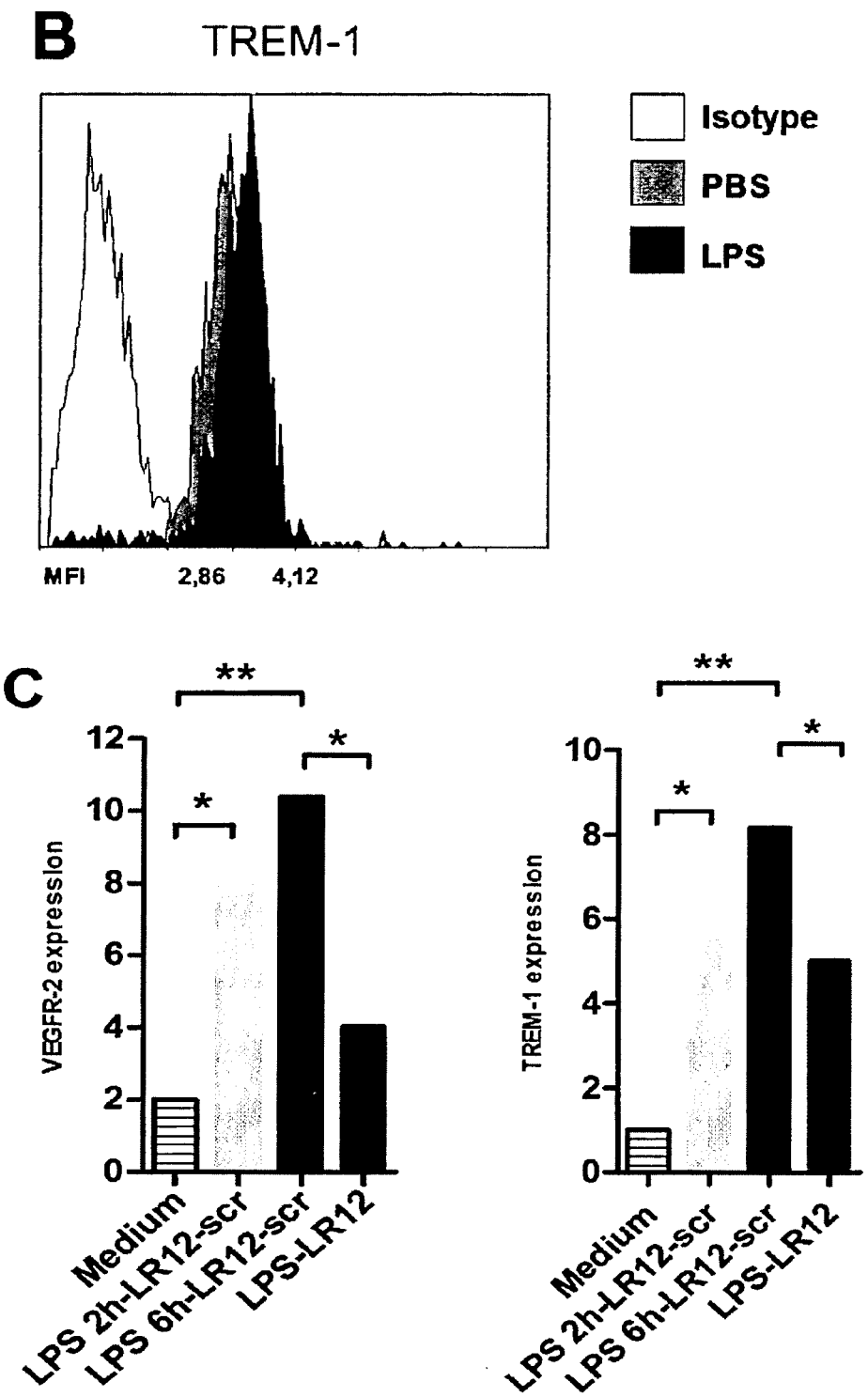

FIG. 3: TREM-1 is constitutively expressed and inducible in microvascular endothelial cells.

CD146+/VEGFR2+ cells isolated from mouse lung and liver (LuMECs and LiMECs) were analysed by flow cytometry for TREM-1 expression. TREM-1 is constitutively expressed on Li/LuMECs (A). TREM-1 expression is inducible in vivo during experimental sepsis (A) or in vitro upon 1 hour stimulation with LPS (B). Kinetics of TREM-1, and VEGFR2 expressions were also analyzed by FACS (C). LPS induced a time-dependent up-regulation of TREM-1 and VEGFR2 expressions, which were prevented by TREM-1- and TLT-1-derived peptides. Data are representative of at least 10 different experiments, p values: *p<0.05, p<0.01, *p<0.001.

Figure 4:
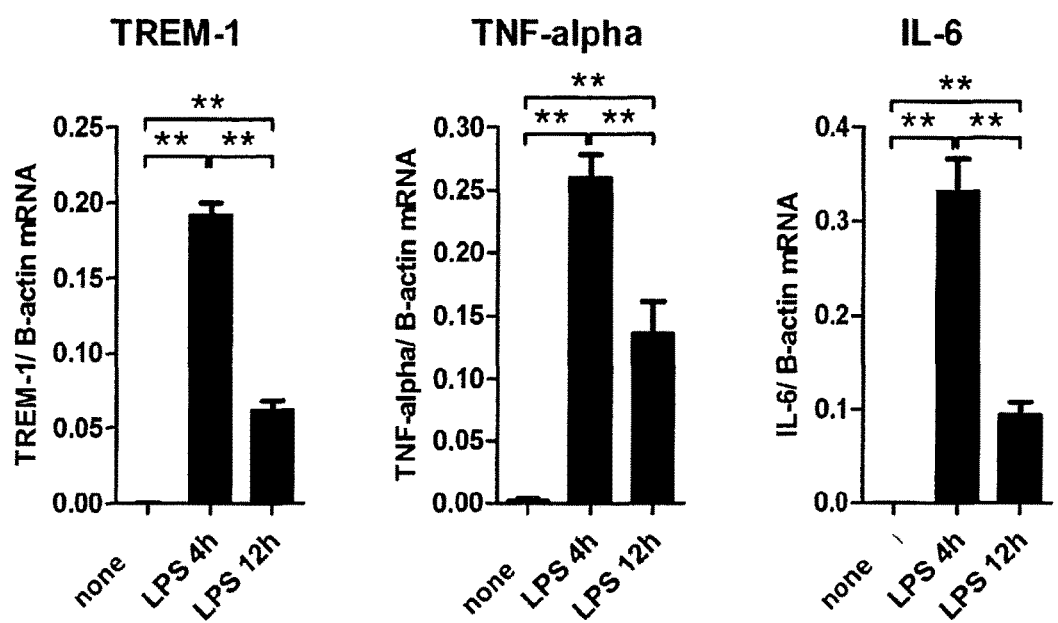

FIG. 4: Kinetics of TREM-1 expression upon LPS stimulation.

(A) In vitro LuMEC (CD 146+, VEGFR2+) were stimulated with LPS for 4 h and 12 h and where analyzed by qRT-PCR for (A) Trem-1, Tnf-α (B) and Il-6 (C) expressions. Data are representative of at least 10 different experiments.

Figure 5:
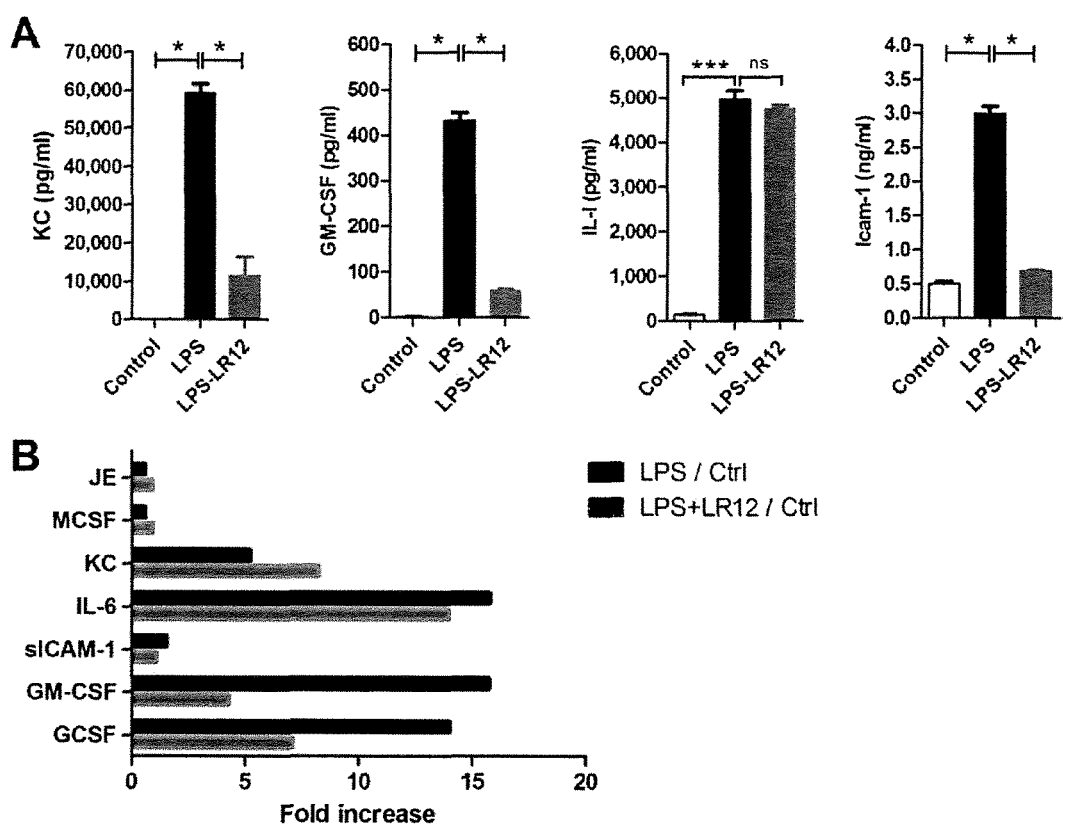

FIG. 5: Effects of TREM-1- and TLT-1-derived peptides on cytokine production by LuMEC stimulated 24 h with LPS.

(A) proteins concentrations in the supernatants of LuMEC stimulated 24 h with LPS were analyzed by ELISA *, P<0.05; , P<0.01.*, P<0.001.

(B) Cytokine/chemokine measurement in LuMEC stimulated for 24 h with LPS. Data are expressed as a ratio between controls and cells treated with TREM-1- and TLT-1-derived peptides (a ratio >1 denotes a higher concentration in controls than in treated cells).

Data are representative of at least 10 different experiments.

Figure 6:
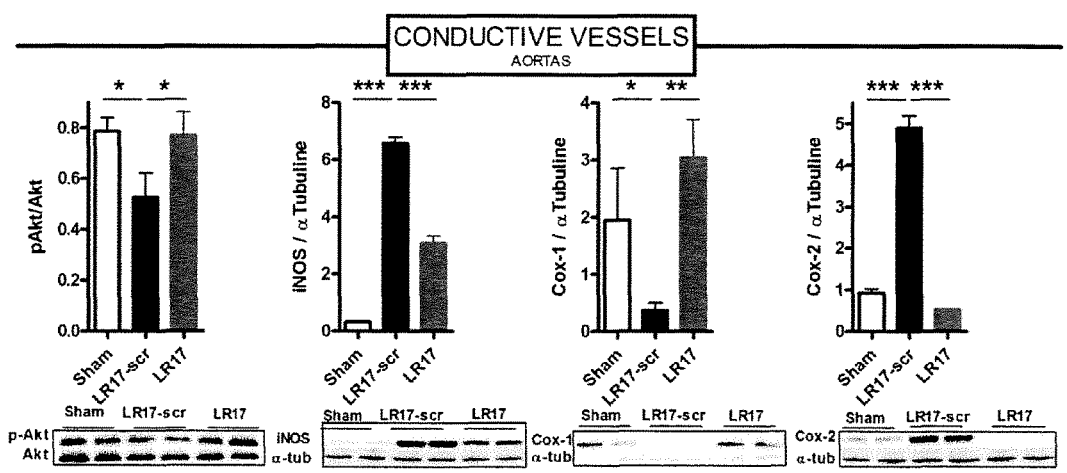
Figure 6:
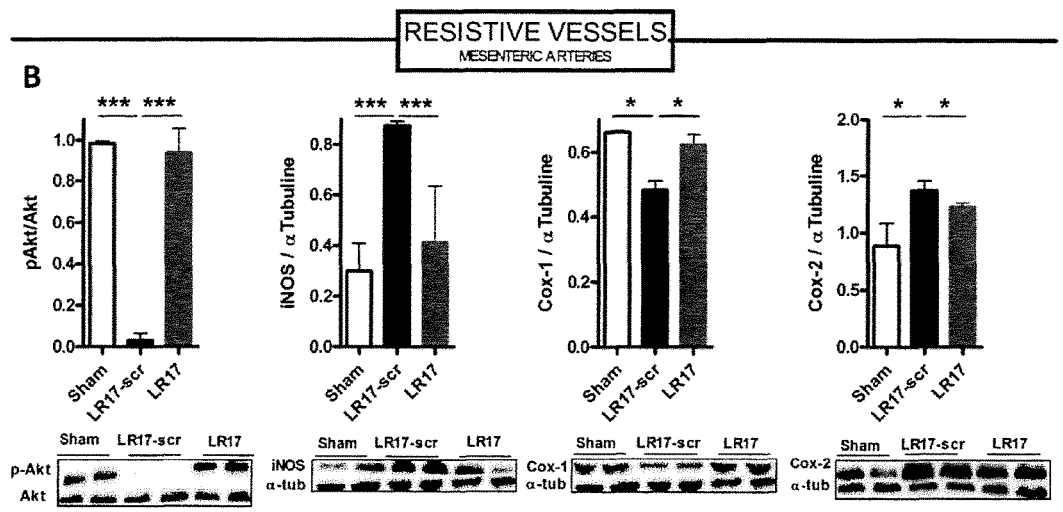

FIG. 6: in vivo impaired vascular intracellular signaling pathways during sepsis are restored with TREM-1 modulation by TREM-1 and TLT-1-derived peptides.

TREM-1- and TLT-1-derived peptides is able to restore an impairment of Akt pathway and Cox-1 expression as well as to restore an upregulation of inductible pathway exemplified by Cox-2 and iNOS. This effect was measured in aortas (A) and mesenteric arteries (B).

Data are representative of at least 5 different experiments, p values: *p<0.05, p<0.01, *p<0.001.

Figure 7:
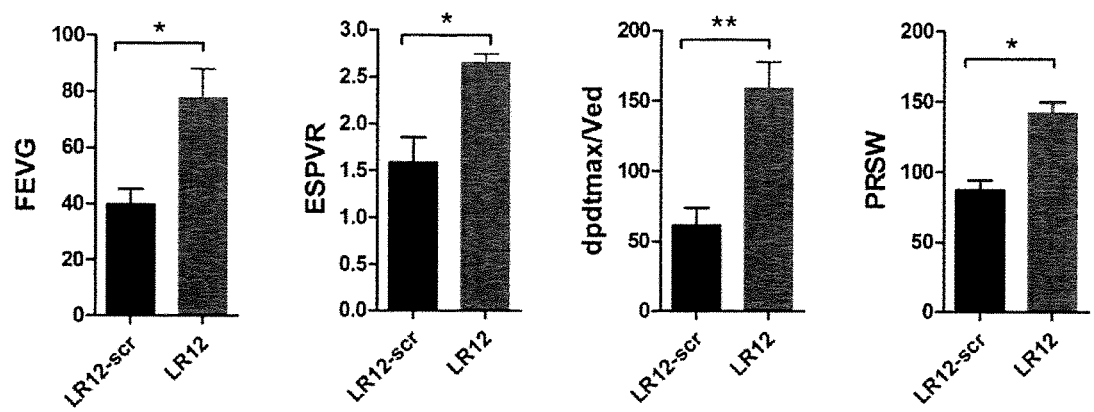

FIG. 7: TREM-1 modulation by TREM-1 and TLT-1-derived peptides is beneficial against sepsis-induced cardiac dysfunction.

TREM-1- and TLT-1-derived peptides administration during rat model of sepsis-induced cardiac dysfunction is associated with an increase of intrinsic cardiac function measured by Millar catheter (FEVG, ESPVR, dpdtmax/Ved, PRSW).

Data are representative of at least 10 different experiments.

Figure 8:
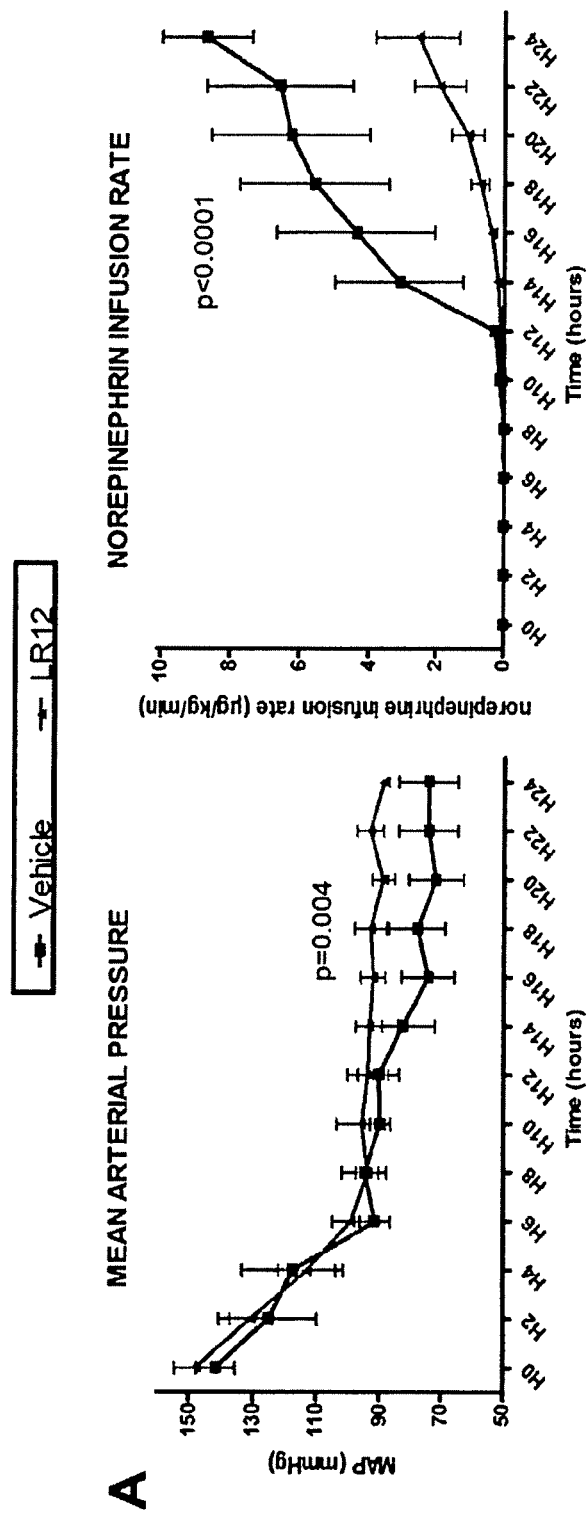
Figure 8:
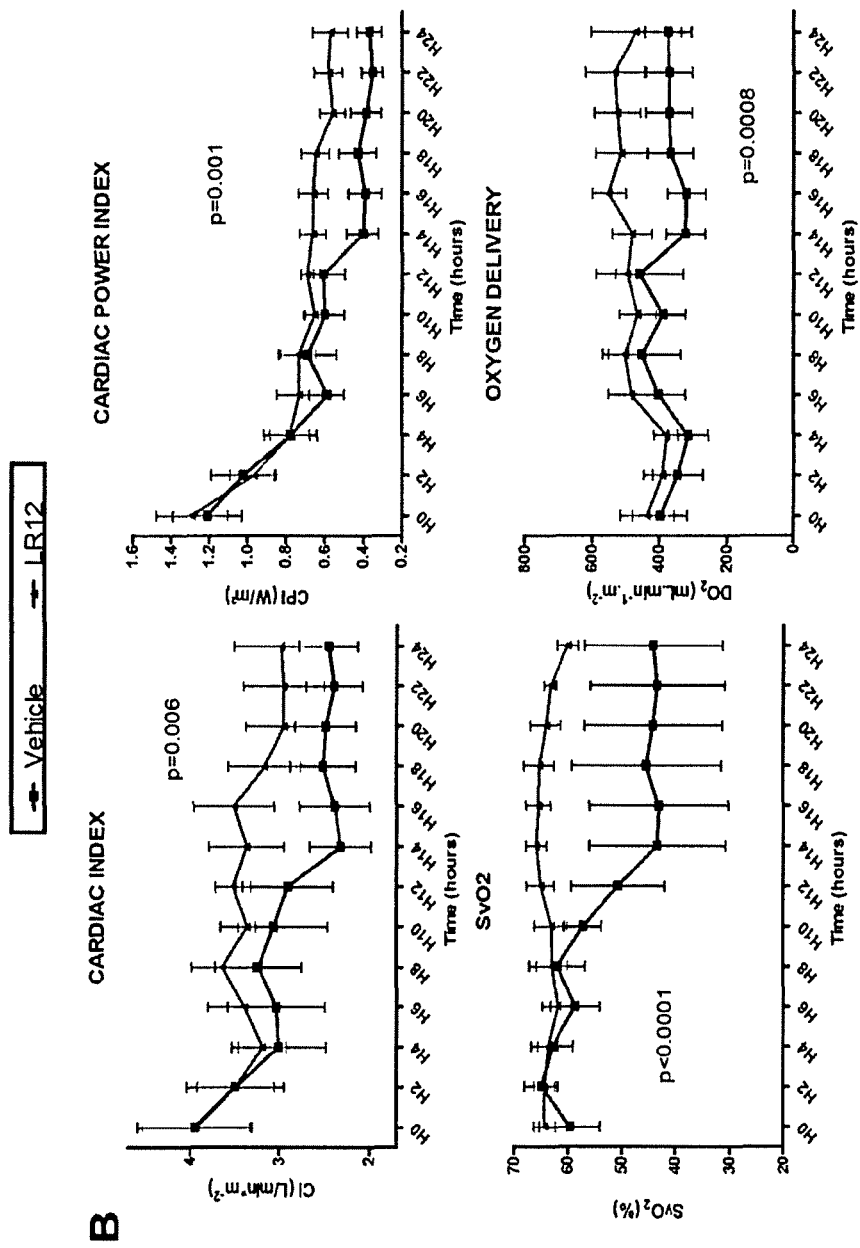
Figure 8:
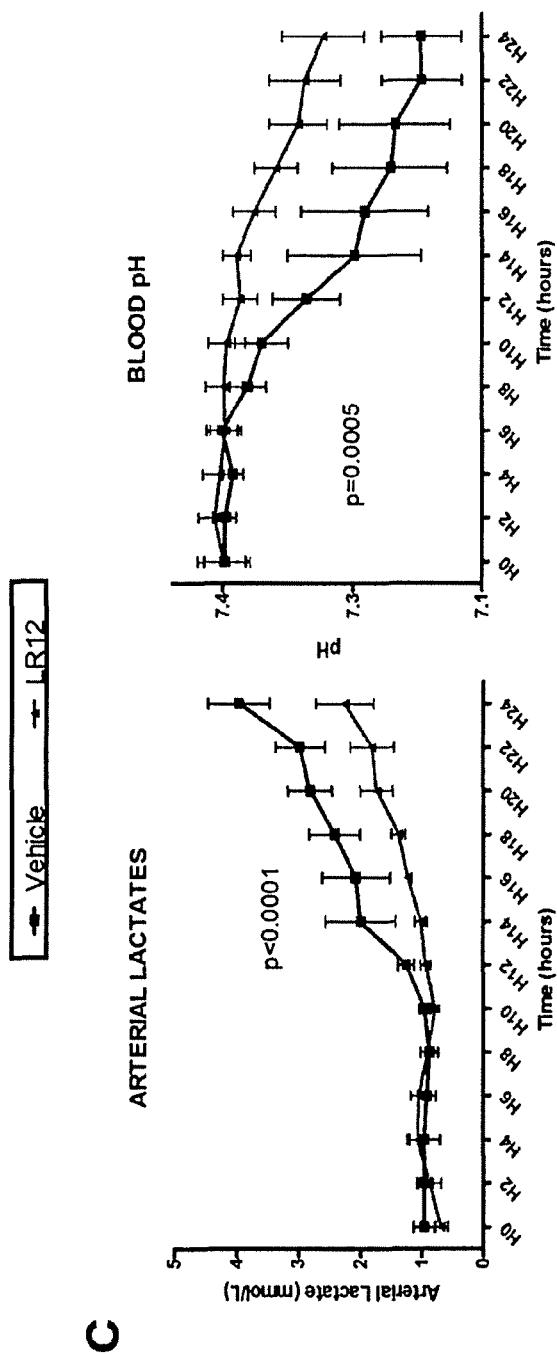

FIG. 8: TREM-1 modulation by TREM-1 and TLT-1-derived peptides is beneficial against sepsis-induced hypotension and cardiac dysfunction.

(A) Administration of TLT-1- and TREM-1-derived peptides during mini-pig model of sepsis-induced cardiac dysfunction is associated with a decrease in norepinephrine infusion needed to maintain a stable mean arterial pressure (85 mmHg). Indeed, MAP was constantly higher and norepinephrine dose lower in TLT-1- and TREM-1-derived peptides treated animals than controls.

(B) Evolution of cardiac index, cardiac power index, SvO2 and oxygen delivery. All these parameters were higher in TLT-1- and TREM-1-derived peptides treated animals than controls.

(C) Development of acidosis and hyperlactatemia were attenuated by LR12.

LR12 group, n=6//LR12-scrambled group n=5.

Figure 9:
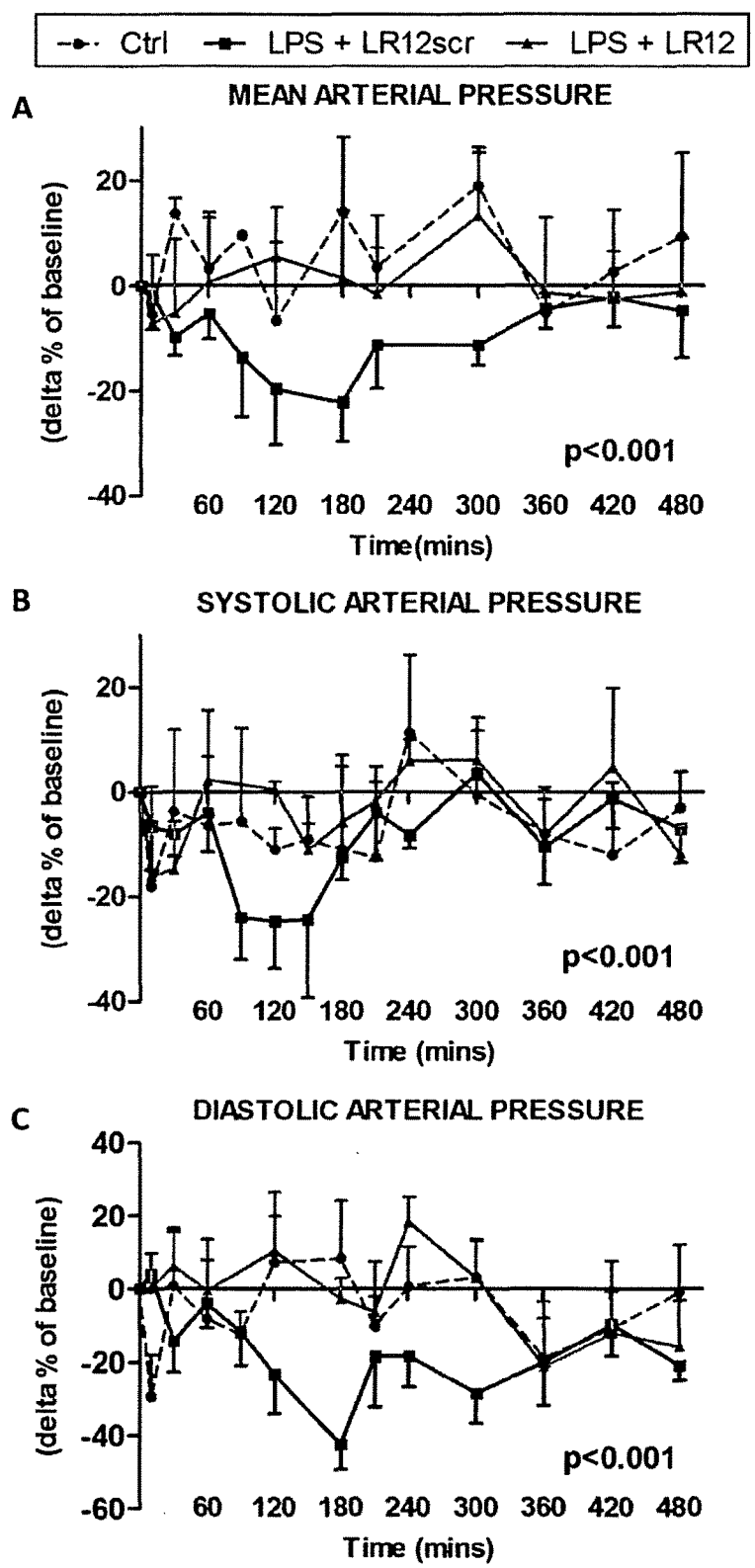

FIG. 9: TREM-1 modulation by TREM-1 and TLT-1-derived peptides is beneficial against sepsis-induced alteration in diastolic, systolic and mean arterial pressure.

Administration of TLT-1- and TREM-1-derived peptides during monkey model of sepsis-induced cardiac dysfunction (endotoxemia) completely prevents endotoxin-induced transient drop in blood pressure (mean (A), systolic (B) and diastolic (C)) ($p<0.001$ control peptide vs LR12). Mean±SD. N=6/group.

Figure 10:
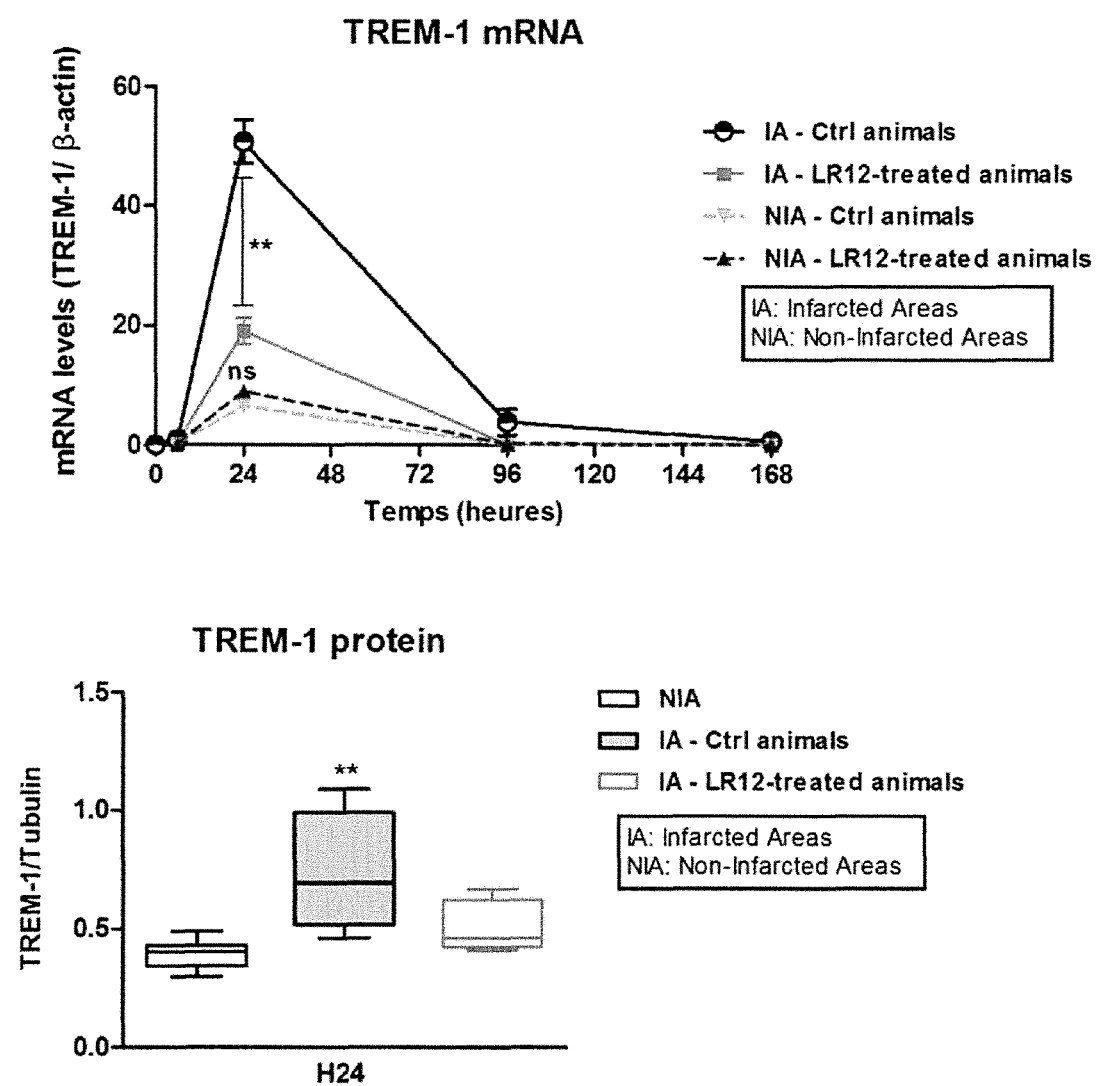

FIG. 10: TREM-1 is expressed in myocardial tissue and is up-regulated during ischemia.

(A) q-PCR mRNA quantification of Trem-1 in the myocardium at baseline and in infarcted areas 6, 12, and 24 hours after myocardial infarction.

(B) Quantification of the TREM-1 protein 24 hours after myocardial infarction.

Data are representative of at least 5 different experiments. Results are mean±SD. p values are *$p<0.001$ [healthy versus infracted areas].

Figure 11:
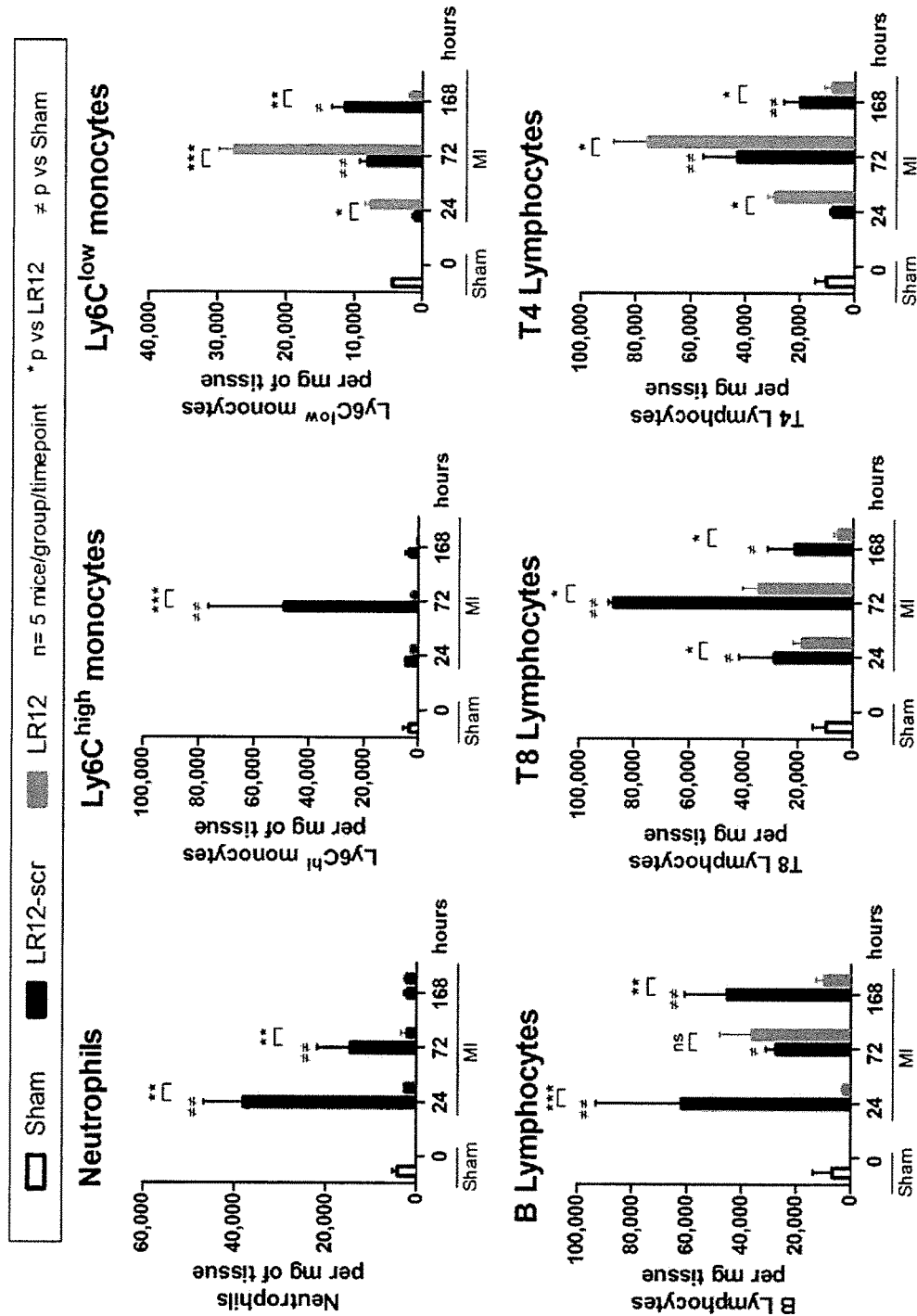
Figure 11:
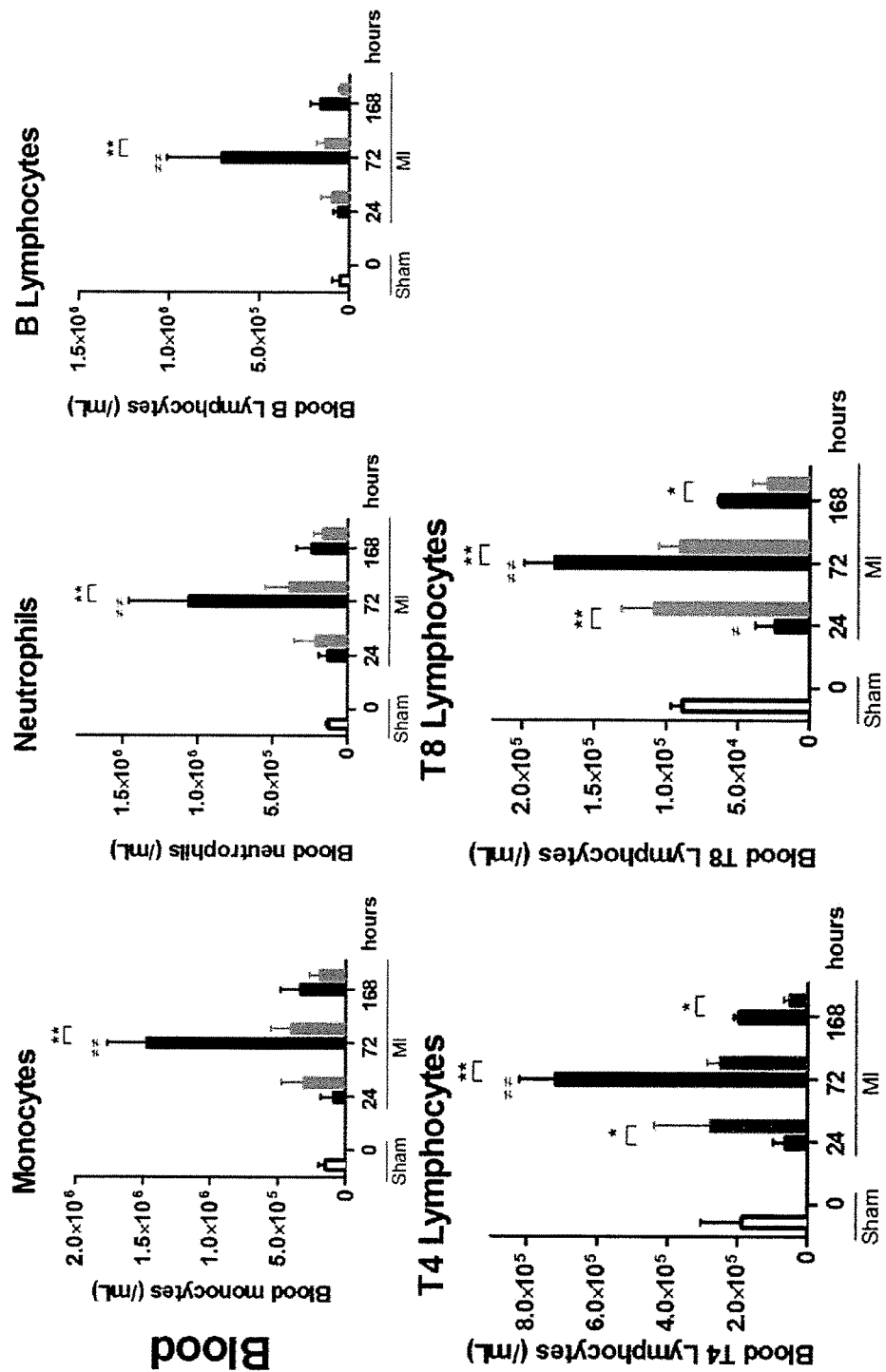
Figure 11:
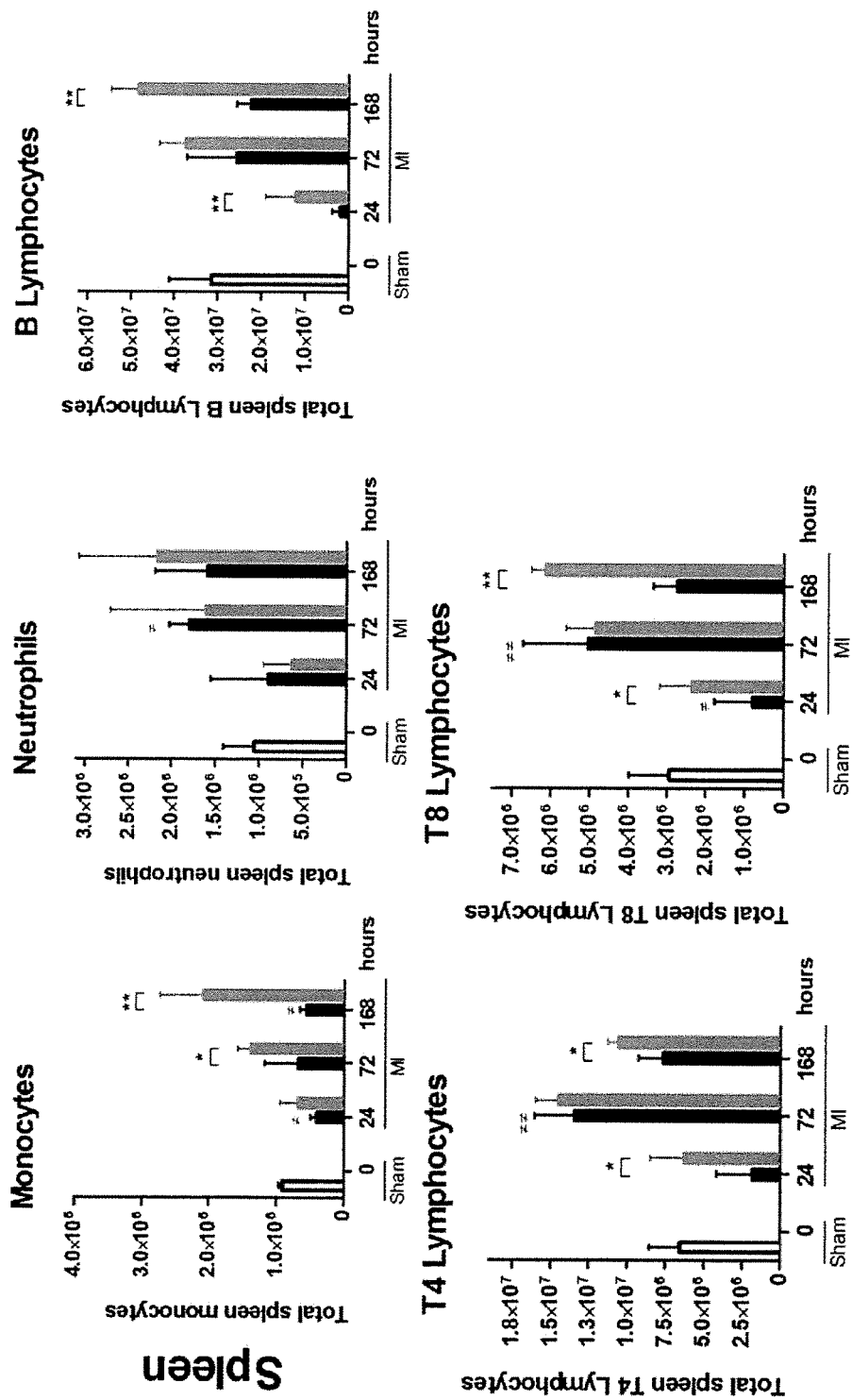
Figure 11:
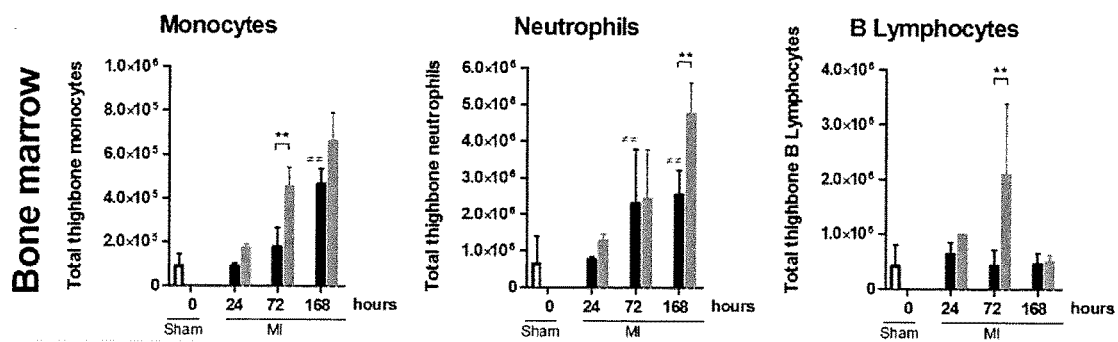
Figure 11:
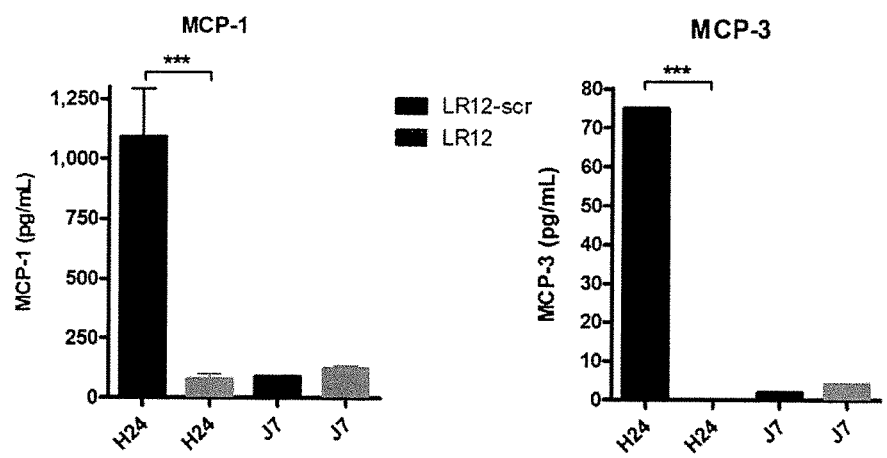

FIG. 11: TREM-1 and TLT-1-derived peptides, by modulating TREM-1, control leukocyte recruitment in infarcted myocardium as well as leukocyte mobilization from remote compartments.

(A) Flow-cytometric quantification of leukocyte infiltration in infarcted myocardium at different time points in mice treated with TLT-1- and TREM-1-derived peptides or the control peptide (LR12-scr); n=5 mice per group and per time point; *$p<0.05$, $p<0.01$, *$p<0.001$ versus LR12-scr, $p<0.05$, $p<0.01$ versus sham.

(B) Flow-cytometric quantification of leukocytes' subtypes in bone marrow, blood, and spleen at different time points after MI; n=6-7 at each time point; *$p<0.001$, $p<0.01$, *$p<0.05$ versus LR12-scr treated mice; ≠≠$p<0.01$, ≠$p<0.05$ versus Sham operated mice.

(C) MCP-1 and MCP-3 plasma concentrations after MI; n=5 mice; ***$p<0.001$ versus LR12-scr treated animals.

Figure 12:
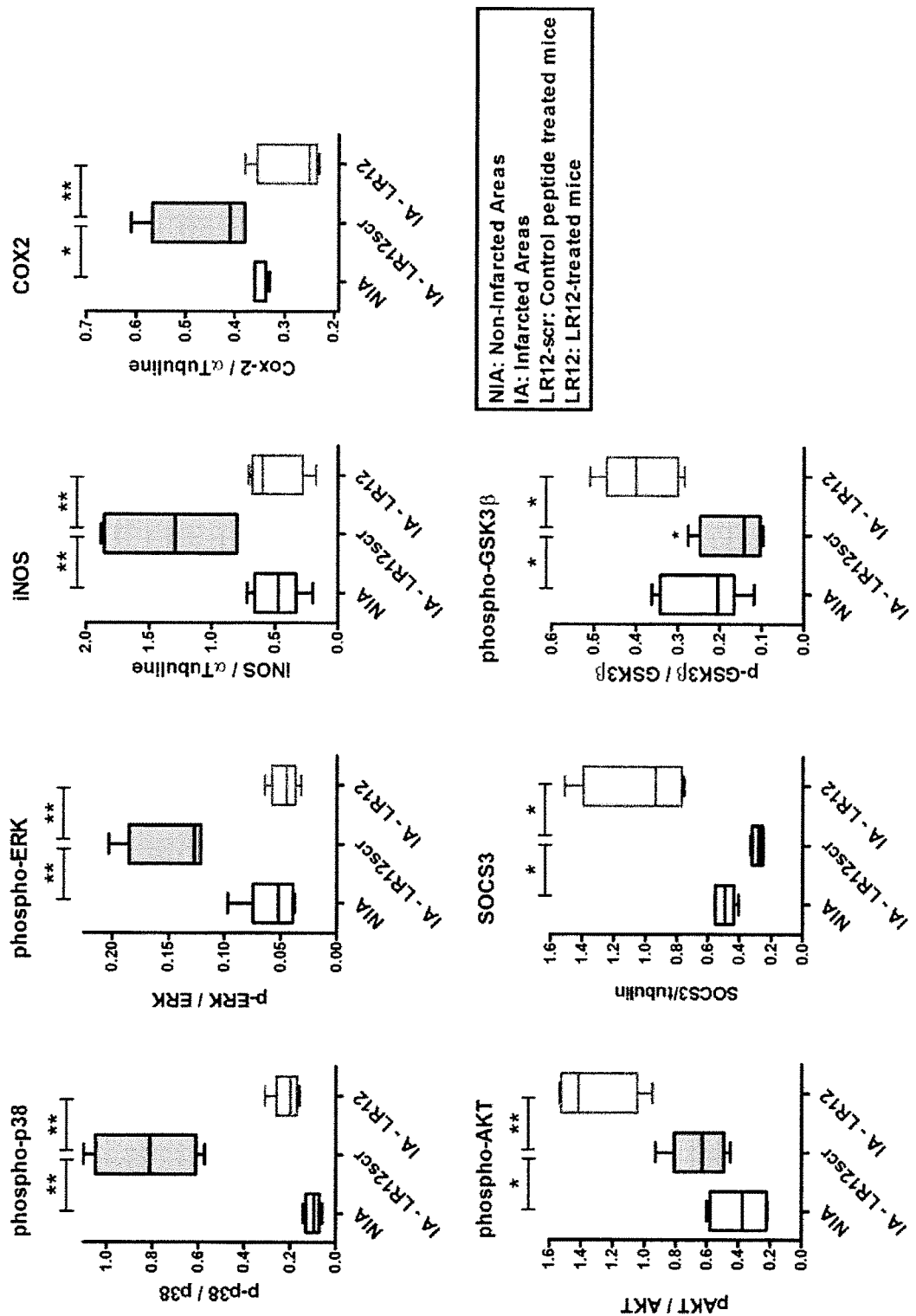

FIG. 12: TREM-1- and TLT-1-derived peptides, by inhibiting TREM-1, modulate myocardial inflammatory reaction during ischemia in mice.

For these experiments, myocardial lysate was obtained 24 hours after the induction of myocardial infarction from mice treated with TREM-1- and TLT-1-derived peptides or control LR12-scrambled peptide ('controls'). Two areas were studied: a healthy area harvested distally from the infarcted zone in a control animal and an infarcted area. Data are representative of at least 5 different experiments. Results are mean±SD. p values are *$p<0.001$ [LR12 versus controls].

Western Blot of lysates of myocardial tissue analysed with antibody to phospho (p)-p38, (p)-ERK1/2, iNOS, Cox2, (p)-Akt, (p)-GSK3β, Socs3.

Figure 13:
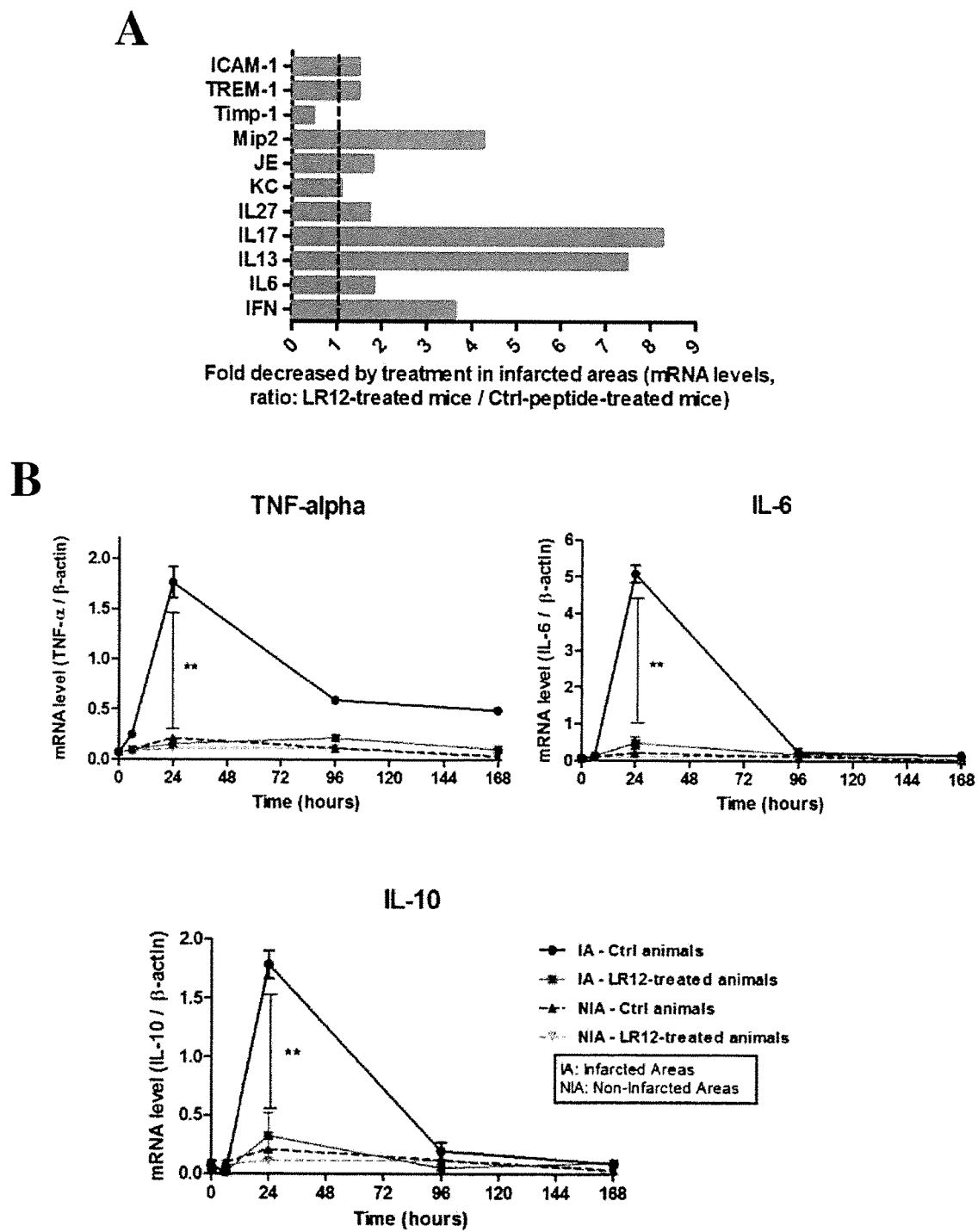

FIG. 13: Effects of TREM-1- and TLT-1-derived peptides on cytokine production by myocardial tissue during ischemia in mice.

For these experiments, myocardial lysate was obtained 6, 24 and/or 96 hours after the induction of myocardial infarction from mice treated with TREM-1- and TLT-1-derived peptides or control LR12-scrambled peptide ('controls'). Infarcted areas were analyzed for cytokine/chemokine production. Data are representative of at least 5 different experiments. p values are *$p<0.001$ [LR12 versus controls].

(A) Cytokine/chemokine measurement in infarcted myocardial tissue 24 hours after myocardial infarction. Data are expressed as a ratio between controls and animals treated with TREM-1- and TLT-1-derived peptides (a ratio >1 denotes a higher concentration in controls than in treated mice).

(B) Cytokines' expression: Tnf-α, Il-6 and IL-10 mRNA levels in infracted myocardial tissue 6, 24, and 96 hours after myocardial infarction.

Figure 14:
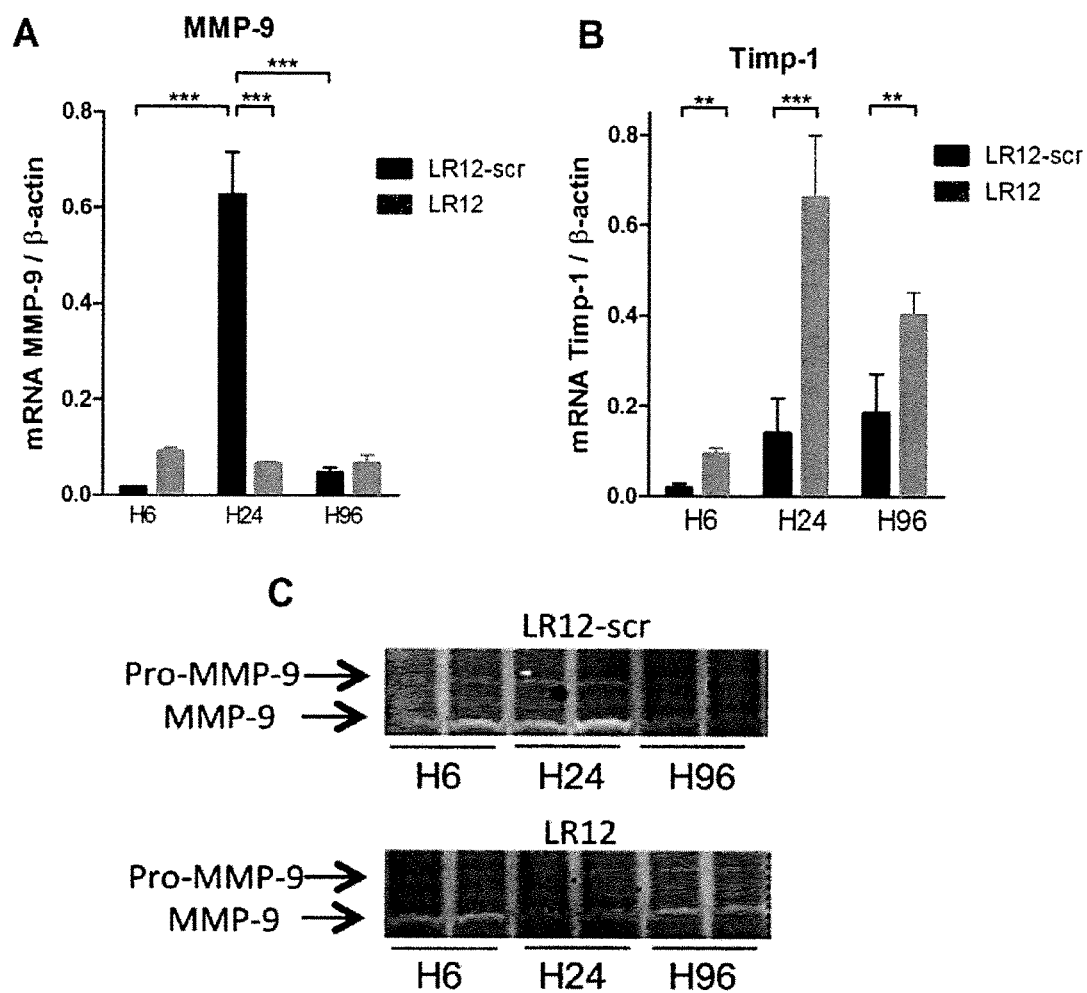

FIG. 14: TREM-1- and TLT-1-derived peptides, by inhibiting TREM-1, decrease protease activity in myocardial infarcted areas.

For these experiments, myocardial lysate was obtained 6, 24 and 96 hours after the induction of myocardial infarction from mice treated with TREM-1- and TLT-1-derived peptides or control LR12-scrambled peptide ('controls'). Infarcted areas were analyzed. Data are representative of at least 5 different experiments.

(A) Q-PCR mRNA quantification of Mmp9;

(B) Timp-1 and;

(C) Representative in-gel zymography reflecting Mmp-9 gelatinase activity at baseline, 12, 24, and 96 hours after myocardial infarction. Up: control-peptide treated animals; down: LR12 treated animals.

Figure 15:
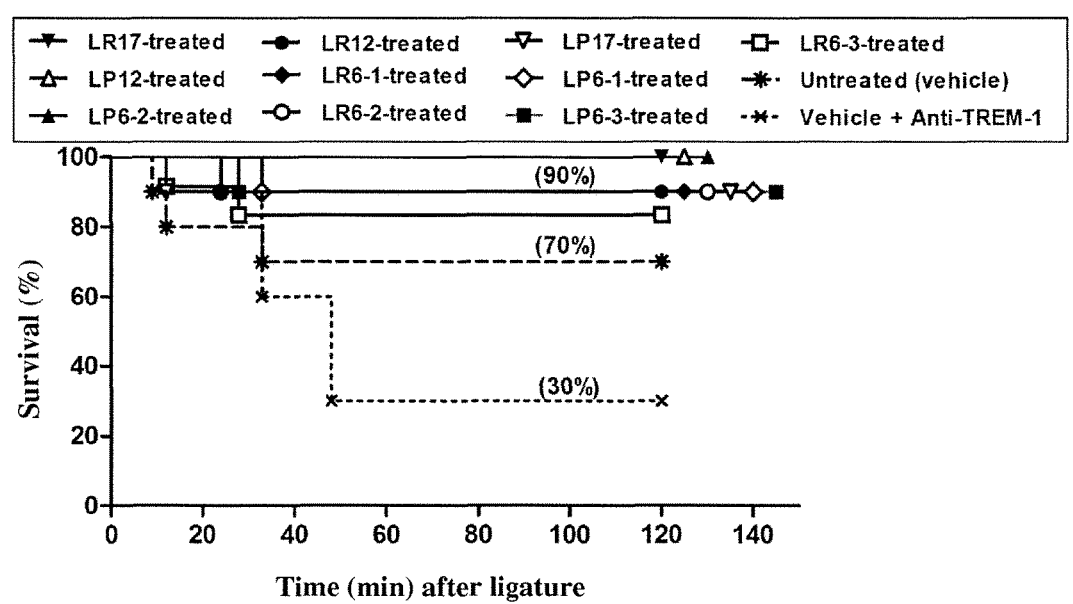

FIG. 15: TREM-1- and TLT-1-derived peptides, by inhibiting TREM-1, improve survival after myocardial infarction in mice.

Adult male Balb/c mice (20-23 g) were subjected to myocardial ischemia and were randomly grouped (n=10-15 per group) to receive repeated TREM-1- and TLT-1-derived peptides (100 µg in 0.2 mL NaCl 0.9% once a day for 5 days), scrambled-LR12 (100 µg in 0.2 mL NaCl 0.9% once a day for 5 days), or 10 µg anti-TREM-1 mAb in 0.2 mL NaCl 0.9% i.p. injections. Survival was monitored over 1 wk and analyzed by Log Rank test. (There were no deaths after the 5th day). Data are representative of at least 15 different experiments.

Figure 16:
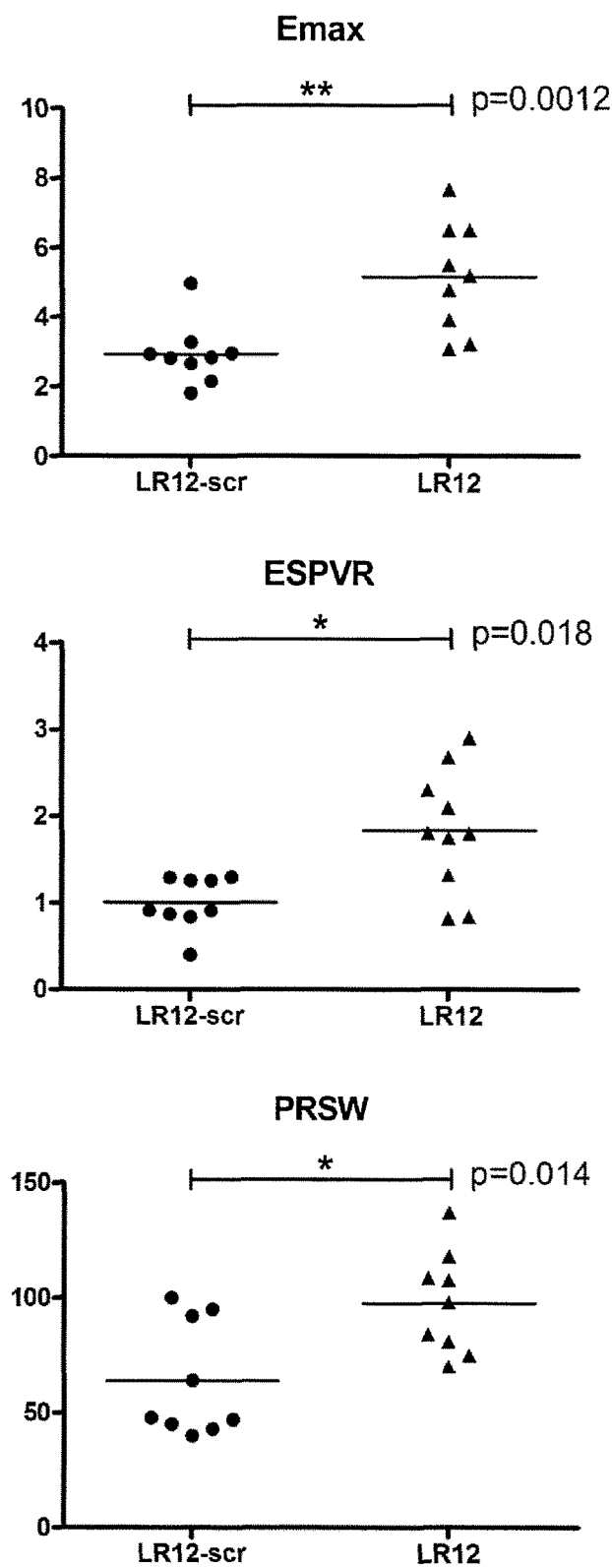

FIG. 16: TREM-1- and TLT-1-derived peptides, by inhibiting TREM-1, improve cardiac function after myocardial ischemia-reperfusion in rats.

Adult male Wistar rats were subjected to myocardial ischemia-reperfusion and were randomly grouped (n=10) to receive repeated TREM-1- and TLT-1-derived peptides (3 mg/kg in 0.2 mL NaCl 0.9% once a day for 5 days) or scrambled-LR12 (3 mg/kg in 0.2 mL NaCl 0.9% once a day for 5 days). Six weeks after myocardial injury, cardiac function was investigated under anaesthesia by using a conductance catheter. Emax, ESPVR, and PRSW were higher in animals treated with TREM-1- and TLT-1-derived peptides than in control rats. All $p<0.02$ [controls versus LR12]).

Figure 17:
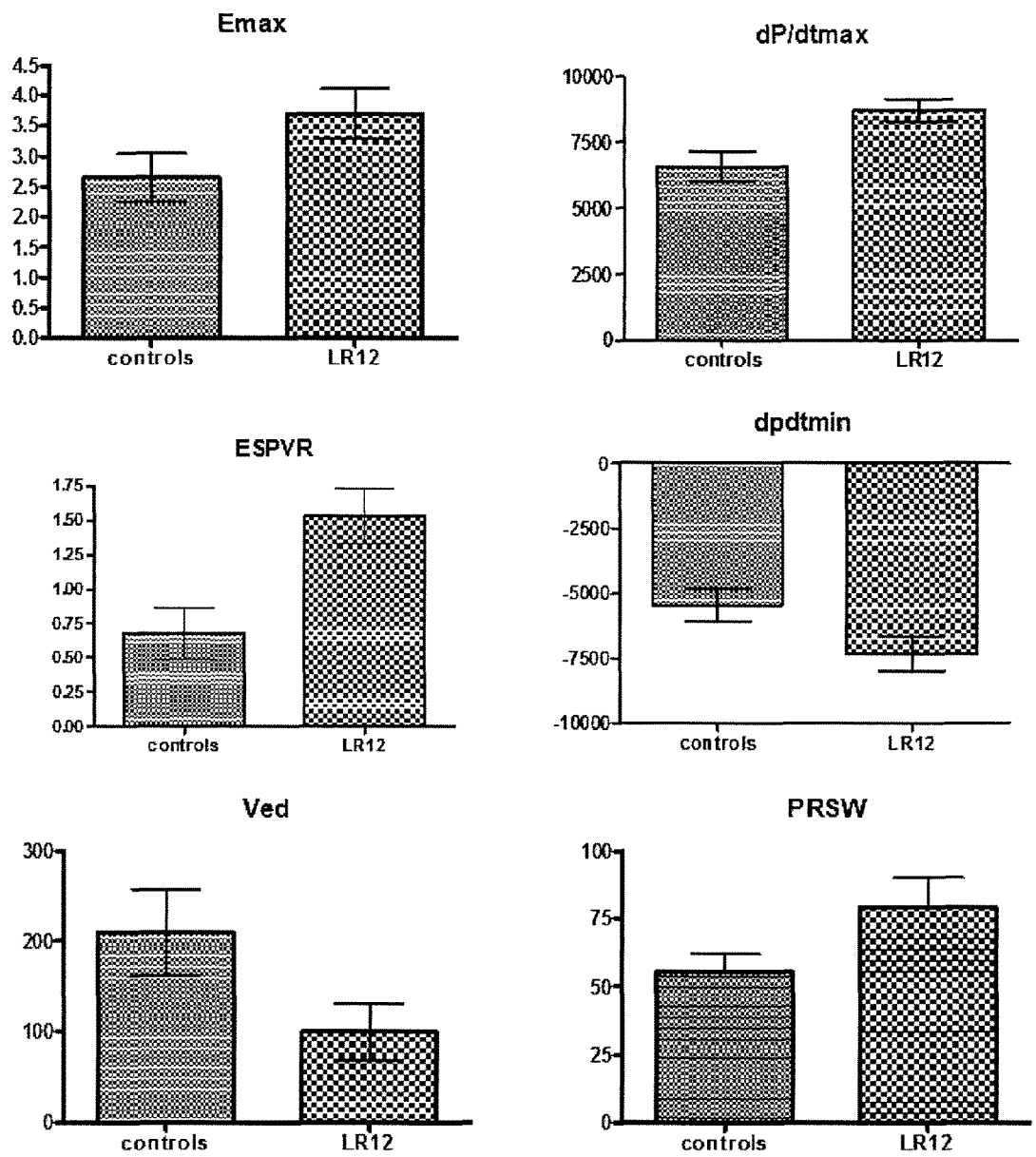

FIG. 17: TREM-1- and TLT-1-derived peptides, by inhibiting TREM-1, improve systolic and diastolic functions after myocardial infarction in rats.

Adult male Wistar rats were subjected to myocardial ischemia and were randomly grouped (n=20) to receive repeated TREM-1- and TLT-1-derived peptides (3 mg/kg in 0.2 mL NaCl 0.9% once a day for 5 days) or scrambled-LR12 (3 mg/kg in 0.2 mL NaCl 0.9% once a day for 5 days). Six weeks after myocardial injury, cardiac function was investigated under anaesthesia by using a conductance catheter. All studied parameters were better in animals treated with TREM-1- and TLT-1-derived peptides than in control rats (all $p<0.01$ [controls versus LR12]).

Figure 18:
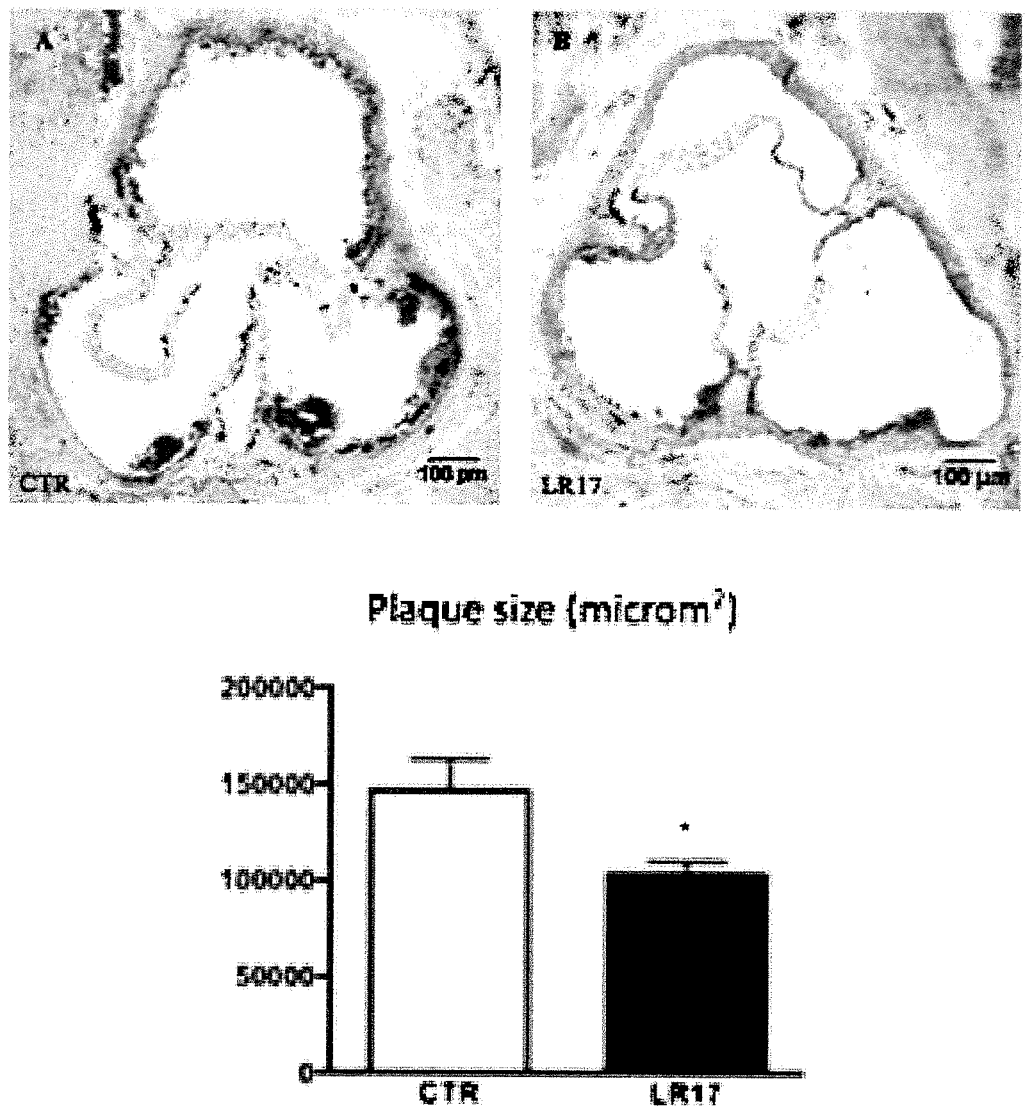

FIG. 18: Atherosclerotic plaques in the aortic sinus form apoE−/− mice treated by daily intraperitoneal injection of PBS (left) or LR12 (right) during 4 weeks.

Treatment with TREM-1- and TLT-1-derived peptides reduces atherosclerosis development in the aortic sinus evaluated using Red Oil staining: 103318 µm² with LR12 treatment versus 146736 µm² with vehicle administration, $P=0.02$. Data are representative of at least 15 different experiments.

Figure 19:
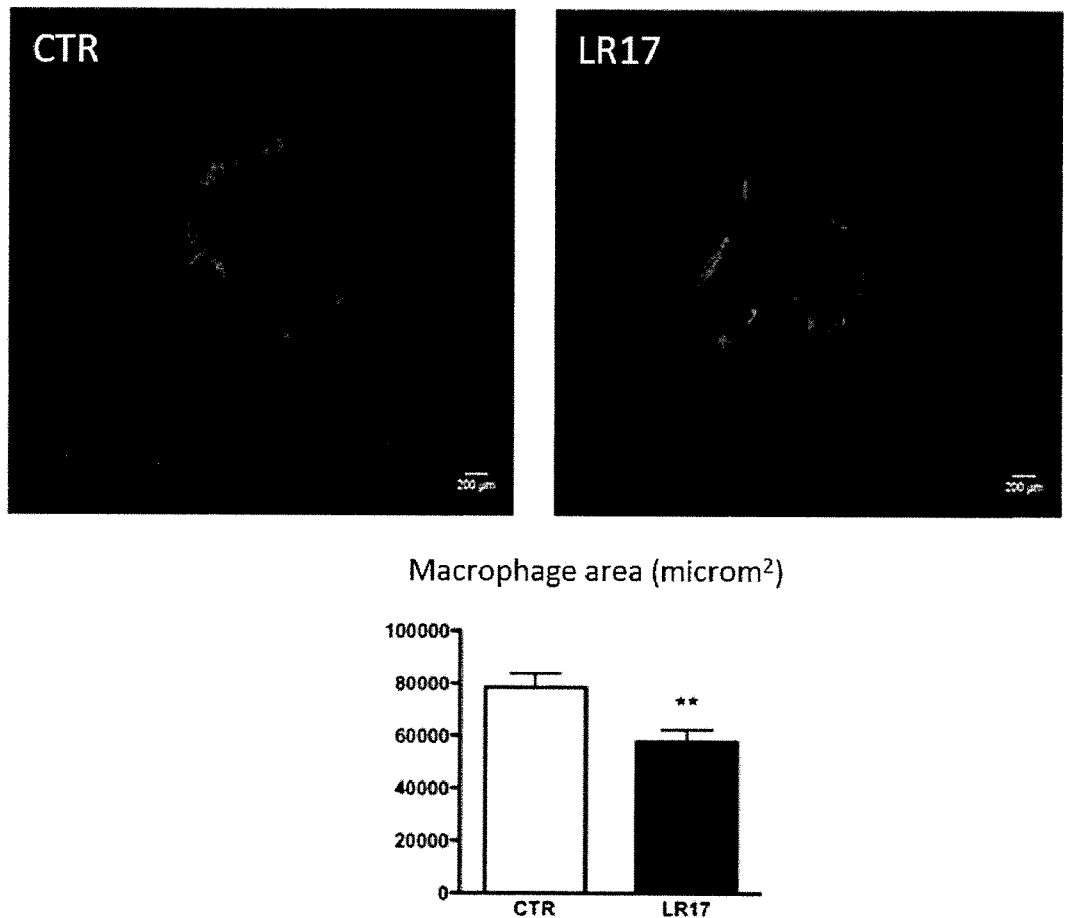

FIG. 19: Macrophage staining (anti-MOMA2, red) in atherosclerotic plaque.

Treatment with TREM-1- and TLT-1-derived peptides in apoE−/− mice reduces macrophage infiltration in atherosclerotic plaques ($p=0.004$) by 27% versus control animals, as quantified by immunofluorescent staining and immunohistochemistry (anti-MOMA2).

Figure 20:
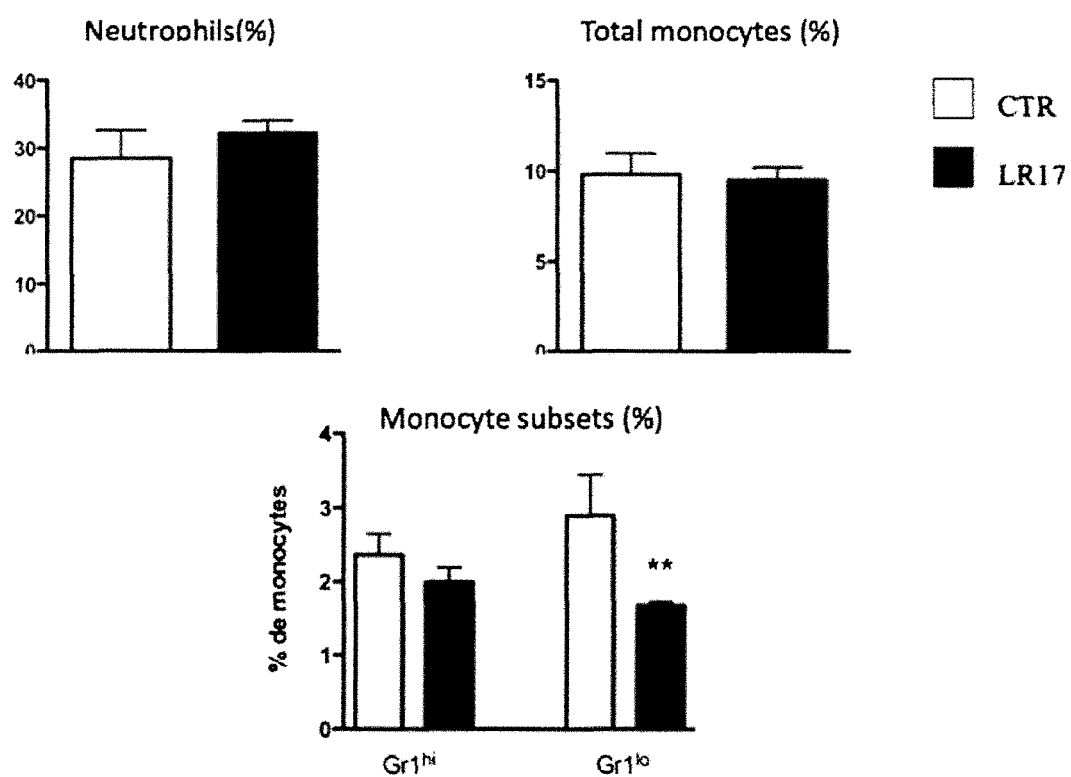

FIG. 20: TREM-1- and TLT-1-derived peptides, by inhibiting TREM-1, induce a reduction of circulating non-classical monocyte population at day 7.

Circulating $CD115^+Gr1^{low}$ and $CD115^+Gr1^{high}$ monocytes were counted after staining by flow cytometry 7 days in a model of atherosclerotic mice. Data are representative of at least 5 different experiments. ($P<0.05$).

Figure 21:
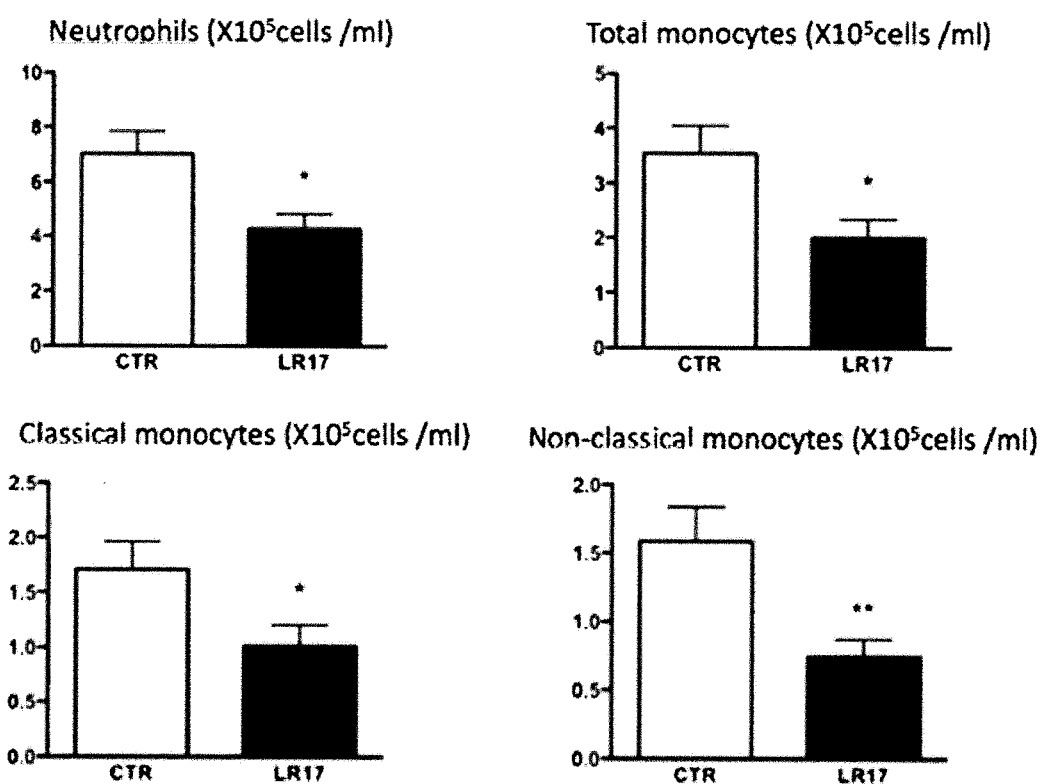

FIG. 21: TREM-1- and TLT-1-derived peptides, by inhibiting TREM-1, reduce leukocytosis at day 28.

Circulating $CD115^+Gr1^{low}$ and $CD115^+Gr1^{high}$ monocytes were counted after staining by flow cytometry 28 days in a model of atherosclerotic mice. Data are representative of at least 5 different experiments. *$p<0.05$; **$p<0.001$.

Figure 22:
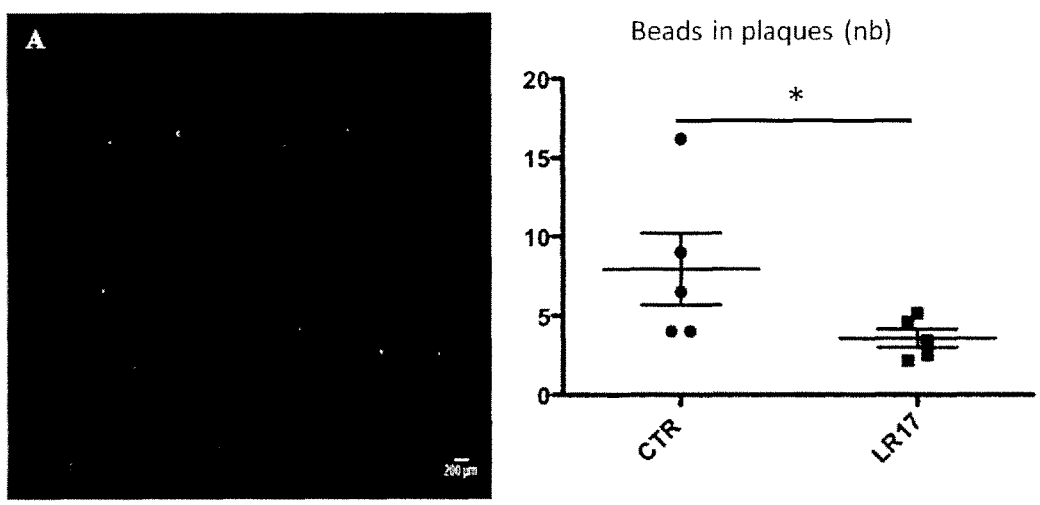

FIG. 22: Treatment with TREM-1- and TLT-1-derived peptides reduces monocytes infiltration within the lesions.

Monocytes were labelled in vivo by retro-orbital IV injection of 1 µm Fluoresbrite green fluorescent plain microspheres diluted 1:4 in sterile PBS. Fluorescent beads count in the lesion reflects monocyte recruitment. Data are representative of at least 5 different experiments. $P<0.05$.

EXAMPLES

Material & Methods
Peptides

Based on the TLT-1 and TREM-1 sequences in GenBank|EMBL|DDBJ (accession numbers AY078502, AF534822, AF241219 and AF287008), TREM-1- and TLT-1-peptides were designed mimicking different parts of their extracellular domains (TREM1-LP17, TREM1-LP12, TREM1-LP6-1, TREM1-LP6-2, TREM1-LP6-3, TLT1-LR17, TLT1-LR12, TLT1-LR6-1, TLT1-LR6-2 and TLT1-LR6-3). They were chemically synthesized (Pepscan Presto BV, Lelystad, The Netherland) as Cter amidated peptides for in vivo assays. The correct peptides were obtained with >99% yields and were homogeneous after preparative purification, as confirmed by mass spectrometry and analytic reversed-phase high-performance liquid chromatography. These peptides were free of endotoxin. Corresponding scrambled peptides were similarly synthesized and served as control peptides.

Animals

All procedures were approved by the local committee for care and use for laboratory animals and were performed according to international guidelines on animal experimentation. Mice and rats were obtained from the Charles River (Strasbourg, France).

Isolation of Mouse Thoracic Aorta and Rat Mesenteric Artery

Animals were anesthetized with an intraperitoneal injection of pentobarbital sodium. A midline abdominal incision was performed, and the thorax opened to expose the thoracic aorta (mice) or the mesenteric artery (rats).

The vessels were emptied from blood and incubated for 20 hours in RPMI medium supplemented with 10% bovine fetal serum and antibiotics. Different conditions were randomly applied: 1) control vessel 2) vessel incubated ex vivo with LPS (10 µg/mL) 3) LPS and peptidic treatment 4) agonistic αTREM-1 (5 µg/mL) 5) de-endothelialized vessels incubated with LPS and treatment.

In some experiments, total RNA and proteins were extracted from the vessels after stimulation.

Vascular Reactivity

Vascular reactivity of aorta was studied on a wire myograph (EMKA Technologies, France). The experiments were performed at 37° C. in a physiological salt solution (PSS) with the following composition: 119 mmol/L NaCl, 4.7 mmol/L KCl, 14.9 mmol/L NaHCO3-, 1.2 mmol/L MgSO42-, 2.5 mmol/L CaCl2, 1.18 mmol/L KH2PO4-, and 5.5 mmol/L glucose, continuously bubbled with 95% O2 and 5% CO2). After an equilibration period (at least 20 minutes) under the optimal passive tension, two successive contractions in response to the combination of KCl depolarization (100 mM) and 10 µM phenylephrine (Phe) (Sigma-Aldrich, Saint Quentin Falavier, France) were used to test the maximal contractile capacity of the vessels. After a 20 min washout period, concentration-response curves to PE were elicited by cumulative administration of this vasoconstrictor agonist (1 nM to 100 µM). After a new washing period, endothelium-dependent relaxation was assessed by testing the relaxing effect of acetylcholine (ACh) (1 nM to 100 µM; Sigma, St Louis, Mo., USA) after a pre-contraction by 1 µM of phenylephrine (Phe). The presence of functional endothelium was confirmed with acetylcholine (1 µM), which elicited a relaxation superior to 50%.

Isolation of Lung and Liver Microvascular Endothelial Cells (LuMEC and LiMEC)

Mice were sacrificed under deep anesthesia (pentobarbital) to harvest lungs and livers. Isolation of mouse lung and liver microvascular endothelial cells was performed according to a previously described protocol [Daqing et al, 1998] with some modifications. Briefly, organs were washed in 10% FBS-DMEM, minced into 1-2 mm squares, and digested with collagenase Type I (2 mg/ml, Gibco) at 37° C. for 1 h with occasional agitation. The cellular digest was filtered through a 70 µm cell strainer, centrifuged at 1,500 rpm and the cells were plated on gelatin-coated dishes containing DMEM/F12 medium (Gibco) supplemented with 20% FBS, 100 µg/ml ECGS (BD Biosciences) and antibiotics. On day 1, the floating cells were removed and washed with PBS and fresh culture medium was added. After 5 days, the first purification of these cells using the CD146 MicroBead Kit was performed. After trypsinization, the cells were resuspended in growth medium and then plated on fresh gelatin-coated dishes. After 15 days cells were subjected to a second purification according to the same procedure. Purity (>85%) and viability of endothelial cells were verified. In addition, with FACS analysis, the cell phenotype was assessed through the determination of VEGFR2 and CD146 expression by flow cytometry.

Mini-Pig Preparation and Monitoring of Sepsis-induced Hypotension and Sepsis-induced Cardiac Dysfunction Adult male mini-pigs (*Sus scrofa domestica*, Vietnamese pot-belied mini-pigs, 30-40 kg) were purchased from Elevage Ferry (Vosges, France). Before surgery, animals were fasted overnight with free access to water. Preanesthesia was performed through intramuscular administration of ketamine (10 mg/kg) and midazolam (0.1 mg/kg). Anesthesia was induced and maintained with intravenous pentobarbital (initial bolus: 10 mg/kg, and continuous administration 6-8 mg/kg/h), intermittent sufentanyl (10 µg), and pancuronium (4 mg) if necessary. Animals were mechanically ventilated (tidal volume 8 ml/kg, PEEP 5 cm H2O, FiO2 0.21, respiratory rate 14-16 breaths/min adjusted to maintain normocapnia). Left jugular vein was exposed and a triple-lumen line was inserted. Right jugular vein was also catheterized and a Swan-Ganz catheter was positioned allowing the continuous recording of cardiac output, SvO2, and right atria and pulmonary arterial pressures. A right carotid arterial catheter was inserted for continuous measurement of arterial pressure. A catheter in the bladder allowed urine collection.

After instrumentation, a midline laparotomy was performed to collect feces from the left colon: 1.5 g/kg were suspended in 200 mL of 0.9% NaCl and incubated at 38° C. for 2 hours. After surgery, a tube was left in place for the peritonitis induction and ascites drainage.

After surgery, animals were allowed to recover for 2 hours before baseline measurements (defined as 'H0'). Normal saline was continuously administered (10 mL/kg/h) throughout the study. Body temperature was kept constant (±1° C.) using heating pads or cooling.

After baseline data collection (H0), peritonitis was induced by administration of autologous feces through the abdominal tube which was subsequently maintained clamped. After 2 hours (H2), animals were randomized to receive LR12 (LR12 group, n=6) or the vehicle (normal saline) alone (Control group, n=5). A bolus of 5 mg/kg (in 60 mL) was intravenously delivered over 30 minutes, then a 1 mg/kg/h (15 mL/h) infusion was started and lasted throughout the study period.

Animal care was then provided by an experienced intensive care physician with strict adhesion to the following guidelines throughout the study period:

i) Hemodynamic targets: the main objective was to maintain mean arterial pressure (MAP) above 85 mmHg. To achieve this goal and in addition to the maintenance 0.9% NaCl administration (7 mL/kg/h), hydroxyethyl starch (up to 20 mL/kg for the entire study period) (HES 130/0.4, Voluven®, Fresenius) was allowed provided that central venous pressure (CVP) and pulmonary artery occlusion pressure (PAOP) was <18 mmHg. When hydroxyethyl starch maximal volume was reached, a continuous infusion of norepinephrine was started up to 10 µg/kg/min.

ii) Respiratory targets: the main objective was to maintain a PaO2/FiO2 ratio >300 and an arterial PaCO2 at 35-45 mmHg. Ventilator settings could thus be modified by increasing inspiratory/expiratory ratio close to 1:1, PEEP up to 15 cm H2O, and respiratory rate up to 30 breaths/min.

iii) Body temperature should be kept constant (±1° C.) using heating pads or cooling.

iv) Intravenous glucose infusion should be administered when necessary to maintain glycemia at 5-7 mmol/L.

Hemodynamic parameters were continuously monitored including MAP, mean pulmonary artery pressure (MPAP), right atrial pressure (RAP), cardiac output (CO), cardiac index (CI), and SvO2. Systemic oxygen delivery (DO2) and systemic oxygen uptake (VO2) were calculated by the Swan-Ganz monitor. Cardiac Power Index (W/m$^2$) was calculated as MAP×CI/451 (24).

Monkeys Preparation and Monitoring of Sepsis-induced Hypotension and Sepsis-induced Cardiac Dysfunction Male cynomolgus monkeys (*Macaca fascicularis*) (2.8 to 3.5 kg, 24 months old, Le Tamarinier, La Route Royale, Tamarin, Mauritius) were used. Animals were fasted the day before LPS challenge but with full access to water. CITox-LAB France Ethical Committee (CEC) reviewed and approved all study plans (Nr CEC: 02221).

Drug Administration and In Vivo LPS Challenge.

Vital signs and weight were recorded the day before LPS challenge. The next morning, baseline clinical laboratory samples were collected, and a baseline set of vital signs was recorded. The drug was administered into the cephalic or saphenous vein via a Teflon catheter. Contralateral vein was used for LPS administration.

Monkeys were randomized to receive LR12 or placebo (n=6 per group). An additional group of 4 was constituted to only receive vehicle (NaCl 0.9%) infusion and served as the control group.

At time point 0, a 15 mins intravenous infusion of LR12 or placebo solution was begun, at the rate of 12 mL/h (5 mg/kg, 10 mins, 2 mL), delivered by a calibrated syringe pump (Harvard Apparatus). A continuous infusion was then administered for further 8 hours at the rate of 2 mL/h (1 mg/kg/h, 8 hours, 16 mL). Just before treatment infusion, an intravenous bolus of LPS (10 µg/kg) was administered over the course of a 10 mins period into the contralateral catheter. Animals remained awake in an upright position in a restraint chairs and continued to fast from food for the whole study duration.

Pulse rate, and blood pressure were monitored every 15 mins for 1 hour, then every 30 mins for 7 hours.

Mouse Model of Myocardial Infarction

All procedures were performed on mice male C57BL/C ranging in age from 6-8 weeks. Mice were anesthetized by an intraperitoneal injection of xylazine (60 mg/kg) and fixed in supine position. The trachea was intubated and ventilated (the tidal volume was 200 µl/25 g and the respiratory rate was 120 breaths/min). After a left thoracotomy, the left coronary artery was identified and ligated with an 8-0 prolene surgical suture at 1.0 mm distal from tip of the left auricle. LAD occlusion was confirmed by a change in myocardial color from red to white in the ischemia area (Left ventricle). The chest was closed and the skin was sutured with 6-0 silk. The animals returned to their cage where they are supervised until their complete recovery.

Mice were monitored after surgery for mortality. Mice were randomized to receive or not peptides (daily ip injection for 5 days, 5 mg/kg) and monitored for survival. Alternatively, mice were sacrificed after 6 h, 24 h, 96 h (n=6 per group) by anesthesia followed with pentobarbital sodium overdose. A median sternotomy was performed followed by excision of the heart and dissection of ischemic and non-ischemic areas. ARN extraction and protein extraction were then performed for RT-PCR, WB, immunohistology, and ELISA analysis.

Flow Cytometry

Microvascular endothelial cells (MECs) from healthy C57BL/6 and septic (CLP) mice were isolated as described and incubated with anti-mouse VEGFR2 and anti-TREM-1 conjugated with FITC and PE for 20 minutes at 4° C. Cells were the washed twice with PBS and were fixed in 0.1% formaldehyde then analyzed in a flow cytometer. As a control, mouse IgG2a isotype was used at the same concentration.

In other experiments MECs were stimulated or not with LPS (0.1 µg/ml) for 2 and 6 h before FACS analysis.

To prepare single-cell suspensions from infarct tissue, hearts were harvested; minced with fine scissors; placed into a cocktail of collagenase I, collagenase XI, DNase I, and hyaluronidase (Sigma-Aldrich); and shaken at 37° C. for 1 h. Cells were then triturated through and centrifuged (15 min, 500 g, 4° C.).

Spleens were removed, triturated in HBSS at 4° C. with the end of a 3-ml syringe, and filtered through 70-µm nylon filters (BD). The cell suspension was centrifuged at 300 g for 10 min at 4° C. Red blood cells were lysed (Red Blood Cells Lysis solution, Miltenyi), and the splenocytes were washed with HBSS and resuspended in HBSS supplemented with 0.2% (wt/vol) BSA. Peripheral blood was drawn via cardiac puncture with citrate solution as anticoagulant, and red blood cells were lysed. Finally, bone-marrow single-cell suspensions were obtained from femurs after flushing them with 1 mL HBSS, filtering through 70-µm nylon filters and centrifugation at 300 g for 10 min at 4° C. Total viable cell numbers were determined from aliquots using a hemacytometer with Trypan blue (BioRad).

Cell suspensions were incubated in a cocktail of mAbs against $CD4^+$ or $CD8^+$ T cells (CD4- or CD8-APC, CD3ϵ-PE, CD45-FITC), B cells (CD19-PE, CD45-FITC), granulocytes (CD45-FITC, Ly-6G-APC), monocytes subsets (CD115-PE, Ly-6C-APC, CD45-FITC), all antibodies from Miltenyi Biotech. Reported cell numbers were calculated as the product of total living cells (total viable leukocytes per ml) and percentage of cells within selected gate, and reported per mg of tissue (heart), per organ (femur and spleen), or per mL (blood). Data were acquired on a FC500 cytometer (Beckman Coulter).

RNA Extraction and Polymerase Chain Reaction Analysis

Total RNAs were extracted from cells or ischemic and non-ischemic areas using RNeasy Plus Mini Kit (Qiagen, Courtaboeuf, France) and quantified with NanoDrop (ThermoScientific) before being retrotranscripted using the iScript cDNA synthesis kit (BioRad) and quantified by quantitative PCR using Qiagen available probes (Quantitect Primers) for mTREM-1, mTNF-α, mIL-6, mMMP-9, mTIMP-1 and mActB. Alternatively, total RNAs were retrotranscripted with $RT^2$ First Strand Kit (SABiosciences, Tebu-bio, Le Perray-en-Yvelines, France) for PCR arrays (Mouse Innate Immune/Endothelial Cells $RT^2$ Profiler PCR Arrays, SABiosciences). All PCRs were performed in a MyiQ Thermal Cycler and quantified by iQ5 software (Qiagen). Gene expression was normalized with ActB.

Protein Phosphorylation Analysis

Tissues from ischemic and non-ischemic areas or MECs were lysed with PhosphoSafe Extraction Reagent (Novagen) and centrifuged for 5 minutes at 16,000 g at 4° C. to collect the supernatant. Protein concentration was determined according to Bradford's method (Pierce). Lysates were then analysed by Western Blot (Criterion XT Bis-Tris Gel, 4-12%, BioRad and PVDF membrane, Millipore), revealed with anti-phospho-p38, -pERK1/2, -pAKT, -pGSK3β, -iNOS, -COX2, -SOCS3, -TREM-1 and corresponding secondary antibody conjugated with horse-radish peroxidase (Cell Signaling) and SuperSignal West Femto Substrate (Pierce). Anti-p38, -ERK1/2, -AKT, -GSK3β, or -Tubulin were used for normalization. A panel of multiple phosphorylated proteins was also studied by immunoblot (Phospho-Kinase Array; R&D Systems). Acquisition and quantitative signals density analyses were done by LAS-4000 imager and Multi-Gauge software (Fujifilm).

Cytokine Concentration Measurement

Cytokines in myocardial lysates (ischemic and non-ischemic areas) and MECs supernatants were measured by ELISA (Mouse Quantikine ELISA kits, R&Dsystems) and cytokines panel assays (Proteome Profiler Mouse Cytokine Array Kit, Panel A, R&Dsystems) according to manufacturers' recommendations.

Zymography

MMP-9 enzymatic activity in tissue extracts was determined by SDS-PAGE gelatin zymography. MMP-9 present in the tissue extracts degrades the gelatine matrix, leaving a clear band after staining the gel for protein. Briefly, homogenized and normalized tissue samples were denatured without reducing agent and separated by electrophoresis in 7.5% SDS-PAGE gel containing gelatin. Gels were then incubated in the presence of Triton x-100 (to renature protein) at room temperature for 2 h and subsequently at 37° C. overnight in a buffer containing 10 mM $CaCl2$, 0.15 M NaCl, and 50 mM Tris (pH 7.5). Thereafter, gels were stained with 0.25% coomassie blue. Analysis and quantification of bands were performed by densitometry.

Rat Model of Myocardial Permanent Ischemia

Adult male Wistar rats (360-380 g) were used. All rats were anaesthetized with ketamine (100 mg/kg, intramuscularly) and mechanically ventilated. After a left thoracotomy, the left coronary artery was identified and ligated with a 6-0 prolene surgical suture. LAD occlusion was confirmed by a change in myocardial color from red to white in the ischemia area (Left ventricle). The chest was closed and the skin was sutured with 6-0 silk. The animals returned to their cage where they were supervised until their complete recovery. The postoperative mortality rate of all rats was 20%.

After surgical LAD occlusion, importance of ischemic area was evaluated by micro-TEP imaging. Animals were then randomized to receive peptide (5 mg/kg) every 24 h for 5 days or placebo (vehicle).

A further evaluation was performed at 6 weeks by micro-TEP imaging and conductance catheter (Millar) in order to study the treatment effect on myocardial remodeling and myocardial function.

Rat Model of Myocardial Ischemia Reperfusion

Animals received same surgery than in permanent ischemia, but with reperfusion of ischemic area by release of the LAD ligation after 60 minutes of ischemia. The same protocol as described above was then applied.

MicroPET Imaging

In all animals, approximately 70 MBq of $^{18}F$-FDG (in a 0.3-0.5 ml volume) was injected intravenously and under a short anaesthesia (1.5-2.5% of isoflurane inhalation) 60 min prior to initiating PET recording. Recording was acquired in list mode under continuous anaesthesia by isoflurane, using a dedicated small animal PET system (Inveon, Siemens, Knoxville, Tenn., USA). The animals were positioned in the prone position and placed on a heating pad to maintain a body temperature within the normal range. The animals were connected to a standard ECG monitor by three electrodes placed on the inner surfaces of limb extremities. Recording times were 20 min for 18F emission and 6 min for 57Co transmission. The coincidence timing window was set to 3.4 ns and the energy window between 350 and 650 keV. Images were reconstructed in 16 cardiac intervals, providing a temporal resolution of 11-15 ms for common heart rate values. Under these conditions, the axial spatial resolution was less than 1.5 mm. In addition, on LV rat phantoms obtained by a stereolithography process, a precise determination of the actual cavity volumes was provided by FDG PET images above the level of 100 μl corresponding to the lower limit for the LV endsystolic volume in adult.

Conductance Catheter Studies

Rats were anaesthetized with isoflurane and a 2 F high-fidelity micro-manometer catheter (SPR-407, Millar Institute, Houston, Tex., USA) was inserted into the LV via the right carotid artery. The Millar catheter was connected to a Harvard Data Acquisition System interfaced with a PC with the AcqKnowledge III software (ACQ 3.2).

Atherosclerosis in Mouse 12-week old male ApoE−/− mice were put on a fat diet (lipids 15%, cholesterol 1.25%, no cholate) and were treated by daily intraperitoneal injection of peptides (100 μg/day) or PBS. After 4 weeks of fat diet, mice were sacrificed for analysis.

Atherosclerotic plaques were stained using Red Oil and quantified in the aortic sinus. Using immunofluorescent staining and immunohistochemistry, we analyzed plaque composition. Finally, we explored the effects of peptide's treatment on monocyte recruitment in the atherosclerotic plaques using the pulse staining technique developed by Potteaux et al. Briefly, monocytes were labelled in vivo by retro-orbital i.v. injection of 1 μm Fluoresbrite green fluorescent plain microspheres diluted 1:4 in sterile PBS [Potteaux et al, 2011]. Fluorescent beads count in the lesions reflects monocyte recruitment.

Results

Figure 1:
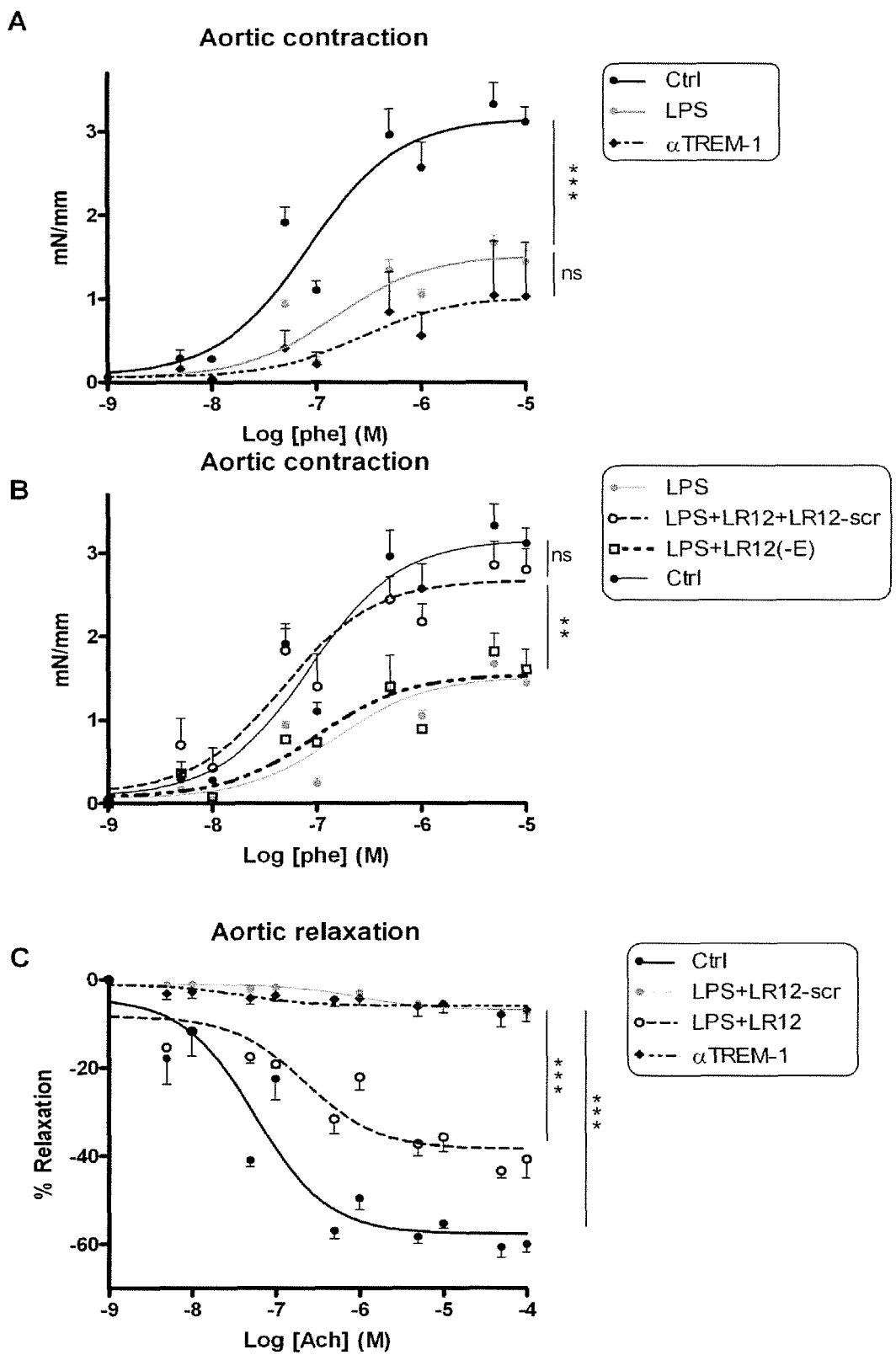
FIG. 1: TREM-1 modulation by TREM-1 and TLT-1 derived peptides is beneficial against vascular dysfunction induced in vitro by αTREM-1 and LPS.

1. TREM-1- and TLT-1-derived Peptides Improve LPS-induced Contractile and Endothelial Dysfunction in Aorta:

To investigate whether TREM-1 modulation could affect directly endothelial vasomotricity, we ex vivo stimulated vessels or desendothelialized vessels dissected from normal rats, with LPS, αTREM-1 (an agonist of TREM-1), TREM-1- and TLT-1-derived peptides and the control peptide LR12-scrambled. First, LPS as well as αTREM-1 induced vasomotricity impairment (FIGS. 1A and C). Then, TREM-1- and TLT-1-derived peptides restored LPS-associated vasomotricity impairment (FIGS. 1B and C). Finally, all TREM-1- and TLT-1-derived peptides lose their beneficial effects when endothelium was removed (FIG. 1B).

2. TREM-1 is Expressed in Endothelial Cells from Aorta and Mesenteric Artery:

To determine whether TREM-1 is expressed in endothelial cells from mouse aorta and rat mesenteric artery, we stimulated vessels (with or without endothelium) with LPS for 6 h (100 ng/ml). Trem-1 expression was up-regulated upon LPS stimulation, only when endothelium was present, both in mouse aorta (FIG. 2A) and rat mesenteric artery (FIG. 2B).

We therefore show for the first time that TREM-1 is expressed on endothelial cells from mouse aorta and rat mesenteric artery.

3. TREM-1 is Expressed on Lung and Liver Microvascular Endothelial Cells (LuMEC and LiMEC):

TREM-1 is constitutively expressed on lung and liver microvascular endothelial cells; its expression is up-regulated during sepsis and by LPS stimulation (FIG. 3). These results were further confirmed by real-time RT-PCR (FIG. 3C).

The expression of Trem-1 was strongly increased after 4 h stimulation with LPS and then decreased thereafter. Similarly, Tnf-α and Il-6 displayed the same kinetics (FIG. 4).

As expected, stimulation of the cells with LPS for 24 h led to a robust production of various cytokines whose concentrations were reduced by TREM-1- and TLT-1-derived peptides (FIG. 5).

Thus, treatment with TREM-1- and TLT-1-derived peptides was able to attenuate the production of pro-inflammatory cytokines by endothelial cells.

4. TREM-1 Modulation Improves Sepsis-induced Cardiovascular Dysfunction:

Mice model: We observed that TREM-1- and TLT-1-derived peptides administration preserved mean arterial pressure and dampened lactic acidosis during septic shock in mice. Exploration of vascular signaling showed that Akt pathway is impaired during sepsis, as well as the expression of Cox-1 in parallel of an up-regulation of Cox-2 and iNOS. These elements, testifying vascular dysfunction, are restored by TREM-1 modulation (FIG. 6).

Rat model: We also focused on intrinsic cardiac function (FIG. 7; Table 2) and showed that TREM-1 modulation by TREM-1- and TLT-1-derived peptides is associated with an improvement of several cardiac parameters: ESPVR (End-Systolic Pressure-Volume Relationship), PRSW (Preload Recruitable Stroke Work), (dP/dt)max/Ved (marker of left ventricular pressure) and LVEF (Left Ventricular Ejection Fraction).

TABLE 2

TREM-1 modulation is beneficial against sepsis-induced cardiac dysfunction.

|  | FEVG | ESPVR | dpdtmax/Ved | PRSW |
| --- | --- | --- | --- | --- |
| Vehicle | 42.1 ± 7.2 | 1.5 ± 0.2 | 55 ± 20 | 79 ± 11 |
| TLT1-LR17 | 75.6 ± 7.2 | 2.5 ± 0.3 | 150 ± 12 | 145 ± 6 |
| TLT1-LR12 | 77.2 ± 9.2 | 2.7 ± 0.1 | 158 ± 18 | 143 ± 7 |
| TLT1-LR6-1 | 79.6 ± 7.4 | 2.9 ± 0.3 | 160 ± 15 | 142 ± 8 |
| TLT1-LR6-2 | 75 ± 5.9 | 2.3 ± 0.2 | 155 ± 12 | 139 ± 10 |
| TLT-1LR6-3 | 78 ± 8.7 | 2.2 ± 0.2 | 157 ± 10 | 149 ± 6 |
| TREM1-LP17 | 75.9 ± 8.9 | 2.7 ± 0.3 | 156 ± 11 | 150 + 8 |
| TREM1-LP12 | 72 ± 9.4 | 2.8 ± 0.2 | 158 ± 18 | 139 ± 6 |
| TREM1-LP6-1 | 76 ± 5.9 | 2.5 ± 0.3 | 150 ± 20 | 145 ± 6 |
| TREM1-LP6-2 | 79.4 ± 9.9 | 2.7 ± 0.1 | 155 ± 15 | 144 ± 6 |
| TREM1-LP6-3 | 78.6 ± 7.4 | 2.9 ± 0.4 | 163 ± 10 | 139 ± 8 |
| TLT-1-LR12scr | 39.9 ± 4.9 | 1.6 ± 0.3 | 61 ± 12 | 88 ± 8 |

Mini-pig model: In a mini-pig model of sepsis, we observed that TREM-1- and TLT-1-derived peptides administration attenuated cardiovascular failure. Peritonitis induced a rapid decline of MAP (FIG. 8A) despite volume rescucitation (7750±540 mL for controls vs. 6500±800 mL for LR12 group, p=0.137). Therefore, in order to maintain MAP >85 mmHg, norepinephrine was started by H12 in 4/5 and 1/6 control and LR12-treated animals respectively. The norepinephrine infusion rate needed to maintain blood pressure was significantly lower in the LR12-treated animals than in controls (FIG. 8A).

Associated to hypotension, both cardiac and cardiac power indexes (believed to better describe cardiac performance) became depressed in the control group. This translated into a progressive decline of SvO2 and DO2 (FIG. 8B). Again, LR12 showed significant beneficial effects in attenuating cardiac failure. Both groups developed a progressive lactic acidosis (FIG. 8C), though largely attenuated by LR12 (p=0.0005).

Monkey model: In a model of endotoxin infusion in monkeys, we observed that TREM-1- and TLT-1-derived peptides administration attenuated cardiovascular failure. Heart rate was transiently increased after LPS injection with no effects of LR12 infusion (not shown). LPS challenge induced a slight increase of body temperature, especially between H1 and H2, but the difference between placebo (LR12scr) and LR12-treated animals was not significant (not shown).

Even if the doses of LPS used were small, transient hypotension developed in the placebo-treated group: systolic arterial pressure decreased up to 25% at 180 mins and diastolic arterial pressure up to 40% (p<0.001 vs. LR12 or Control groups). By sharp contrast, LR12 treated monkeys never went hypotensive and their arterial pressure did not differ from control animals (FIG. 9).

5. TREM-1 is Expressed in Myocardial Tissue and is Up-regulated during Ischemia:

To determine whether TREM-1 is expressed in cardiac tissue, myocardium was harvested from mice before coronary ligature and then at 6, 24 and 96 hours after myocardial infarction (MI) both from healthy and infarcted areas. Baseline expression of trem-1 was very low whereas ischemia induced a progressive up-regulation of is expression with a highest level reached 24 hours after MI (FIG. 10A). The same kinetics was observed at the protein level by western blot (FIG. 10B). By contrast, TREM-1 expression remained low in non-infarcted ('healthy') areas at all times (data not shown).

6. TREM-1- and TLT-1-derived Peptides Modulate Leukocyte Recruitment during MI in Mice and Regulate Leukocyte Mobilization from Remote Compartments:

In mouse, and probably in humans too, 2 different monocyte subtypes exist: Ly-6$C^{high}$ monocytes are potent inflammatory mediators, while Ly-6$C^{low}$ monocytes possess opposite effects [NAHRENDORF et al, 2007]. Trem-1 modulation by TREM-1- and TLT-1-derived peptides completely abrogated infiltration of infarcted myocardium by Ly-6$C^{high}$ monocytes, while transiently increased Ly-6$C^{low}$ monocytes recruitment. PMN infiltration was also blocked by LR12 treatment (FIG. 11A). Although TREM-1 is not expressed by lymphocytes, Trem-1 modulation influenced B- and T-cells mobilization: B- and $CD8^+$-lymphocyte infiltration was reduced, while $CD4^+$-cells recruitment was increased in LR12-treated mice.

As Trem-1 seems important in regulating leukocyte recruitment to the infarcted myocardium, we investigated its effect on cellular mobilization from remote compartments. Following myocardial infarction, monocytes egress from the spleen within 24 hours to infiltrate the heart (SWIRSKI, et al.). This phenomenon was observed here with a rapid decrease of spleen monocytes content lasting up to 1 week after MI. Concomitantly, a pronounced elevation of circulating monocytes number was present at 72 hours, while a progressive accumulation occurred in the bone marrow (BM) (FIG. 11B). Trem-1 deletion or modulation almost completely abrogated splenic monocytes depletion as well as blood monocytosis.

Peripheral blood neutrophils count was increased at 72 hours and returned to baseline by 7 days. This neutrophilia was not observed in Trem-1-knockout or LR12 treated mice. Spleen did not seem to be a great contributor for neutrophils production/release as their splenic content barely changed. A progressive and modest accumulation in BM was also observed, with no differences between groups (FIG. 11B).

B-, $CD4^+$-, $CD8^+$-lymphocyte numbers were drastically reduced in the spleen 24 hours after MI, with a concomitant $CD4^+$ and $CD8^+$ lymphopenia. Then increased number of circulating lymphocytes was present at 72 hours before returning to baseline 7 days after MI. Blocking Trem-1 prevented from this lymphocytes kinetics patterns (FIG. 11B).

Monocyte chemoattractant protein 1 (MCP-1 or CCL2), CX3CL1 (or Fractalkine), and MCP-3 (or CCL7) are important chemokines involved in the recruitment of respectively Ly-6$C^{high}$, Ly-6$C^{low}$ monocytes, and lymphocytes to inflammatory sites. Plasmas concentrations of MCP-1, CX3CL1, and MCP-3 were increased 24 hours following MI. MCP-1 and MCP-3 levels were markedly reduced in treated mice (FIG. 11C).

7. TREM-1- and TLT-1-derived Peptides Modulate Myocardial Inflammatory Reaction during MI in Mice:

We next investigated whether TREM-1 modulation by TREM-1- and TLT-1-derived peptides may regulate infiltrating inflammatory cells activation. Inflammatory cells that rapidly invade myocardium following MI activate with the phosphorylation of p38 MAPK, and ERK 1/2, along with an up-regulation of iNOS and COX2 expression. This activation was partly abrogated by TREM-1- and TLT-1-derived peptides (FIG. 12). When we analyzed the kinetics of phosphorylation/expression of these proteins, peptides decrease their levels at all times (not shown). By contrast, several proteins involved in survival (AKT) or known to dampen inflation (SOCS3) were up-regulated by all peptides. For example, Glycogen synthase kinase 3 (GSK3β) plays a pivotal role in regulating the production of pro- and anti-inflammatory cytokines. In innate immune cells, GSK3β inactivation (through phosphorylation) suppresses the production of cytokines and is known to improve cardiomyocyte survival. Here we observed that the phosphorylation of GSK3β was increased by TREM-1- and TLT-1-derived peptides as compared to controls.

As cellular pro-inflammatory activity seemed to be modulated by TREM-1- and TLT-1-derived peptides, we next investigated whether it would translate into a decrease cytokine/chemokine production.

Among the 168 genes involved in innate immunity or endothelial function we examined next, the expression of 156 was altered in the myocardium after coronary artery ligation, mostly at 24 hours after MI. LR12 administration opposed to myocardial infarction-induced gene activation.

As expected, MI led to a robust production of various cytokines (IL6, IL13, IL17, IL27, IFNγ) and chemokines (MIP2, JE). The concentration of these proteins was reduced by TREM-1- and TLT-1-derived peptides (FIG. 13A). Quantitative PCR confirmed these results at the gene level (FIG. 13B), especially after 6 hours of MI.

Thus, TREM-1- and TLT-1-derived peptides administration was able to modulate MI-inflammatory reaction in infarcted areas.

8. TREM-1- and TLT-1-derived Peptides Decrease Protease Activity in Myocardial Infarcted Tissue:

Infiltrating neutrophils and macrophages express matrix metalloproteinase 9 (Mmp-9) in the infarcted myocardium. Mmp-9 activity may be counterbalanced by tissue inhibitor of metalloproteinase-1 (Timp-1). The maintenance of the delicate balance of these 2 proteins plays a crucial role to prevent ventricular remodelling that will lead to cardiac insufficiency. Here we observed that Mmp-9 and Timp-1 mRNA expression increased in the infarcted areas of control mice. By contrast, Mmp-9 expression remained low in animals treated with TREM-1- and TLT-1-derived peptides whereas Timp-1 was impressively up-regulated (FIG. 14A, B). Therefore, the ratio Mmp-9/Timp-1 was constantly higher in control mice. Mmp-9 gelatinase activity in the infarcted areas was constantly greater in controls than in mice treated with TREM-1- and TLT-1-derived peptides (FIG. 14C).

These results support the hypothesis that TREM-1- and TLT-1-derived peptides may play a beneficial role in preserving cardiac architecture and in opposing to cardiac remodelling after MI.

9. TREM-1- and TLT-1-derived Peptides Improve Survival after MI in Mice:

We next wanted to elucidate whether administration of TREM-1- and TLT-1-derived peptides could have some protective effects during MI. Adult male Balb/c mice were i.p. administered randomly with repeated doses (100 µg daily for 5 days) of TREM-1- and TLT-1-derived peptides, or LR12-scrambled beginning 60 min after the permanent coronary artery ligation. All but 1 LR12-treated animals survived (FIG. 15) whereas 40% of control mice died (Log-Rank test; p<0.01). Similar results were obtained with the other TREM-1- and TLT-1-derived peptides.

To investigate whether a sustained TREM-1 engagement could be even more deleterious, we administered mice with an agonistic anti-TREM-1 mAb. This treatment dramatically increased the mortality rate with only 20% survivors.

10. TREM-1- and TLT-1-derived Peptides Improve Cardiac Function after Myocardial Ischemia-reperfusion in Rats:

To investigate the role of TREM-1- and TLT-1-derived peptides in a more relevant model of MI, we performed a transient coronary artery ligation (ischemia-reperfusion model: IR) in rats. After randomisation, animals were then imaged under anaesthesia (micro-TEP) and administered with TREM-1- and TLT-1-derived peptides (3 mg/kg daily for 5 days i.p.) or LR12-scrambled peptide. Imaging was then repeated at 6 weeks before we studied cardiac function by using a conductance catheter (Millar).

At day 1, just after the IR, both groups were comparable. Infarcted areas were moderately important and cardiac function was slightly altered. At 6 weeks, all rats have improved with an almost complete infarction healing and no ventricular remodelling (Table 3). Therefore, TREM-1- and TLT-1-derived peptides had no effect in the parameters assessed by micro-TEP. By contrast, when cardiac function was investigated by a conductance catheter, we observed that TREM-1- and TLT-1-derived peptides dramatically improved crucial systolic parameters such as Emax or PRSW (FIG. 16; Table 4).

TABLE 3

Summary of physiologic parameters during myocardial ischemia-reperfusion in rats.

| | Controls (n = 10) | LR12 (n = 9) | P Value |
|---|---|---|---|
| Baseline | | | |
| Body weight (g) | 410 ± 91 | 391 ± 9 | 0.53 |
| Systolic blood pressure (mmHg) | 136 ± 4 | 134 ± 2 | 0.10 |
| Heart rate (bpm) | 338 ± 42 | 343 ± 43 | 0.78 |
| MI Areas (% of LV) | 42 ± 28 | 41 ± 20 | 0.90 |
| EDV (µL) | 486 ± 74 | 511 ± 55 | 0.41 |
| ESV (µL) | 270 ± 59 | 251 ± 75 | 0.56 |
| EF (%) | 44 ± 7 | 47 ± 6 | 0.47 |
| Six weeks | | | |
| Body weight (g) | 459 ± 63 | 439 ± 12 | 0.37 |
| difference with baseline | 49 ± 18 | 48 ± 10 | 0.17 |
| Systolic blood pressure (mmHg) | 170 ± 5 | 167 ± 6 | 0.16 |
| difference with baseline | 34 ± 3 | 33 ± 6 | 0.73 |
| Heart rate (bpm) | 350 ± 55 | 370 ± 25 | 0.36 |
| difference with baseline | 12 ± 23 | 27 ± 22 | 0.28 |
| MI Areas (% of LV) | 5 ± 10 | 3 ± 9 | 0.63 |
| difference with baseline | −37 ± 15 | −38 ± 8 | 0.61 |
| EDV (µL) | 560 ± 58 | 620 ± 34 | 0.11 |
| difference with baseline | 74 ± 37 | 109 ± 55 | 0.13 |
| ESV (µL) | 251 ± 50 | 273 ± 47 | 0.18 |
| difference with baseline | −19 ± 8 | 22 ± 18 | 0.47 |
| EF (%) | 55 ± 8 | 56 ± 5 | 0.73 |
| difference with baseline | 11 ± 8 | 9 ± 7 | 0.74 |

TABLE 4

TREM-1- and TLT-1-derived peptides improve cardiac function after myocardial ischemia-reperfusion in rats.

| | Emax | ESPVR | PRSW |
|---|---|---|---|
| Vehicle | 2.8 ± 0.3 | 1 ± 0.2 | 68 ± 11 |
| TLT1-LR17 | 5.1 ± 0.6 | 2 ± 0.2 | 105 ± 6 |
| TLT1-LR12 | 4.8 ± 0.5 | 2.2 ± 0.1 | 103 ± 5 |
| TLT1-LR6-1 | 4.5 ± 0.6 | 2.4 ± 0.4 | 102 ± 6 |
| TLT1-LR6-2 | 6.5 ± 0.9 | 1.8 ± 0.1 | 99 ± 8 |
| TLT-1LR6-3 | 5.2 ± 0.4 | 1.7 ± 0.3 | 109 ± 6 |
| TREM1-LP17 | 5.9 ± 0.8 | 2.2 ± 0.3 | 110 ± 5 |
| TREM1-LP12 | 4.5 ± 0.4 | 2.3 ± 0.4 | 99 ± 4 |
| TREM1-LP6-1 | 5.5 ± 0.4 | 2 ± 0.3 | 105 ± 6 |
| TREM1-LP6-2 | 6 ± 0.6 | 2.2 ± 0.1 | 104 ± 5 |
| TREM1-LP6-3 | 5.8 ± 0.5 | 2.3 ± 0.4 | 99 ± 8 |
| TLT-1-LR12scr | 2.7 ± 0.3 | 1.1 ± 0.3 | 65 ± 8 |

Thus, even during this relatively mild model of myocardial ischemia, administration of TREM-1- and TLT-1-derived peptides was able to restore systolic cardiac function.

11. TREM-1- and TLT-1-derived Peptides Improve Systolic and Diastolic Functions after Myocardial Infarction in Rats:

We finally investigated whether the modulation of the inflammatory response conferred by TREM-1- and TLT-1-derived peptides was able to translate into cardiac function improvement after a severe MI. We performed a permanent coronary artery ligation in rats before randomisation and imaging as described above.

Once again, at day 1, both groups were perfectly similar. At 6 weeks, an important cardiac remodelling has taken place as assessed by the presence of an important ventricular dilation. This cardiac remodelling was, at least in part, altered by TREM-1- and TLT-1-derived peptides (Table 5). As an indirect marker of cardiac insufficiency, control animals gained more weight than rats treated with all the peptides.

TABLE 5

Selected physiologic parameters after myocardial infarction in rats.

| | Controls (n = 18) | LR12 (n = 17) | P Value |
|---|---|---|---|
| Baseline | | | |
| Body weight (g) | 303 ± 42 | 313 ± 51 | 0.32 |
| Systolic blood pressure (mmHg) | 134 ± 15 | 136 ± 17 | 0.76 |
| Heart rate (bpm) | 378 ± 39 | 400 ± 26 | 0.07 |
| MI Areas (% of LV) | 23 ± 9 | 22 ± 11 | 0.88 |
| MT Areas (mm²) | 57 ± 27 | 54 ± 30 | 0.88 |
| EDV (µL) | 431 ± 75 | 417 ± 92 | 0.30 |
| ESV (µL) | 223 ± 51 | 215 ± 62 | 0.23 |
| EF (%) | 48 ± 8 | 48 ± 9 | 0.81 |
| Six weeks | | | |
| Body weight (g) | 447 ± 28 | 426 ± 49 | 0.26 |
| difference with baseline | 144 ± 44 | 113 ± 51 | 0.05 |
| Systolic blood pressure (mmHg) | 135 ± 15 | 136 ± 17 | 0.76 |

TABLE 5-continued

Selected physiologic parameters after myocardial infarction in rats.

|  | Controls (n = 18) | LR12 (n = 17) | P Value |
|---|---|---|---|
| difference with baseline | −9 ± 23 | −12 ± 26 | 0.37 |
| Heart rate (bpm) | 372 ± 37 | 393 ± 23 | 0.03 |
| difference with baseline | −6 ± 31 | −8 ± 22 | 0.91 |
| MI Areas (% of LV) | 15 ± 9 | 16 ± 11 | 0.81 |
| difference with baseline | −8.2 ± 5.9 | −6.0 ± 8.1 | 0.11 |
| MI Areas (mm$^2$) | 48 ± 29 | 49 ± 40 | 0.81 |
| difference with baseline | −9 ± 20 | −5 ± 23 | 0.11 |
| EDV (µL) | 704 ± 93 | 615 ± 161 | 0.007 |
| difference with baseline | 273 ± 77 | 198 ± 95 | 0.007 |
| ESV (µL) | 365 ± 77 | 313 ± 128 | 0.02 |
| difference with baseline | 143 ± 60 | 99 ± 80 | 0.06 |
| EF (%) | 49 ± 7 | 50 ± 8 | 0.61 |
| difference with baseline | 0 ± 8 | 2 ± 7 | 0.44 |

When cardiac function was investigated by a conductance catheter, we observed that TREM-1- and TLT-1-derived peptides dramatically improved crucial systolic and diastolic parameters such as Emax, ESPVR, PRSW, dP/dTmin, dP/dTmax, and Ved (FIG. 17).

Taken together, these data support a protective role of TREM-1- and TLT-1-derived peptides in preventing cardiac remodeling and insufficiency following a myocardial infarction.

12. TREM-1- and TLT-1-derived Peptides Prevent Atherosclerosis Development in Mouse:

Atherosclerotic plaques were stained using Red Oil and quantified in the aortic sinus. Interestingly, treatment with TREM-1- and TLT-1-derived peptides induced a significant 30% reduction of the lesion size in the aortic sinus (103318 µm2 versus 146736 µm2, P=0.02) (FIG. 18). This result was confirmed in a second set of experiment.

13. TREM-1- and TLT-1-derived Peptides Alter Atheromatous Plaque Cellular Composition:

Using immunofluorescent staining and immunohistochemistry, we analyzed plaque composition. We didn't observe any difference regarding lymphocyte infiltration (anti-CD3 antibody) and collagen accumulation (Sirius Red) between groups. However, we found a significant 27% reduction of macrophage infiltration within the atherosclerotic lesions from mice treated by TREM-1- and TLT-1-derived peptides (FIG. 19).

14. TREM-1- and TLT-1-derived Peptides Modified Blood Leukocytes Population in Atherosclerotic Mice:

Using flow cytometry, we analyzed blood leucocyte populations. Classical monocytes were CD115+Gr1high and non-classical monocytes were CD115+Gr1low. In apoE−/− mice under a chow diet, only non-classical monocytes expressed TREM. Interestingly, high fat diet increased TREM-1 expression on non-classical monocytes (data not shown).

Then, we analyzed blood leucocyte populations during treatment. At day 7, we observed a significant reduction of non-classical monocytes in the blood of mice treated with TREM-1- and TLT-1-derived peptides (FIG. 20). At day 28, we observed a significant reduction of classical and non-classical monocytes in the blood (FIG. 21).

15. TREM-1- and TLT-1-derived Peptides Decrease Monocytes Recruitment to Atherosclerotic Plaques:

Finally, we explored the effects of treatment with TREM-1- and TLT-1-derived peptides on monocyte recruitment in the atherosclerotic plaques. We used the pulse staining technique developed by Potteaux et al. Briefly, monocytes were labeled in vivo by retro-orbital i.v. injection of 1 µm Fluoresbrite green fluorescent plain microspheres diluted 1:4 in sterile PBS [Ait-Oufella H. et al., 2011]. Fluorescent beads count in the lesions reflect monocyte recruitment. Beads were injected 24 hours before the sacrifice of treated apoE−/− mice. Interestingly, we found a significant reduction of monocyte infiltration in the group treated by TREM-1- and TLT-1-derived peptides compared to the control group (FIG. 22).

REFERENCES

Throughout this application, various references describe the state of the art to which this invention pertains. The disclosures of these references are hereby incorporated by reference into the present disclosure.

Ait-Oufella H, Taleb S, Mallat Z, Tedgui A. Recent advances on the role of cytokines in atherosclerosis. Arterioscler Thromb Vasc Biol 31 (5):969-979 (2011).

Bjorkbacka H, Kunjathoor V V, Moore K J, Koehn S, Ordija C M, Lee M A, Means T, Halmen K., Luster A D., Golenbock D T., Freeman M W. Reduced atherosclerosis in MyD88-null mice links elevated serum cholesterol levels to activation of innate immunity signaling pathways. Nat Med 10 (4):416-421(2004).

Daqing W. Hartwell, Tanya N. Mayadas, Gaëtan Berger, Paul S. Frenette, Helen Rayburn, Richard O. Hynes, Denisa D. Wagner. Role of P-selectin cytoplasmic domain in granular targeting in vivo and in early inflammatory responses. Journal of Cell Biology; 143 4:1129-1141 (1998).

Derive M, Bouazza Y, Sennoun N, Marchionni S, Quigley L, Washington V, Massin F, Max J P, Ford J, Alauzet C, Levy B, McVicar D W, Gibot S. Soluble TREM-like transcript-1 regulates leukocyte activation and controls microbial sepsis. J Immunol. 2012 Jun. 1; 188(11):5585-92. Epub 2012 May 2.

Entman M. L., Smith C. W. Postreperfusion inflammation. A model for reaction to injury in cardiovascular disease. Cardiovasc Res 9:1301-1311 (1994).

Hara H, Saito T. CARD9 versus CARMA1 in innate and adaptive immunity. Trends in Immunology; 30:234-242 (2009).

Harjot K Saini, Yan-Jun Xu, Ming Zhang, Peter P Liu, Lorrie A Kirshenbaum, Naranjan S Dhalla. Role of tumour necrosis factor-alpha and other cytokines in ischemia-reperfusion-induced injury in the heart. Exp Clin Cardiol. 2005 Winter; 10(4): 213-222.

Libby P. Inflammation in atherosclerosis. Nature 420 (6917):868-874 (2002).

Mehta J. L., Li D. Y. Inflammation in ischemic heart disease: response to tissue injury or a pathogenetic villain. Cardiovasc Res; 2:291-299 (1999).

Nahrendorf M, Swirski F K, Aikawa E, Stangenberg L, Wurdinger T, Figueiredo J L, Libby P, Weissleder R, Pittet M J. The healing myocardium sequentially mobilizes two monocyte subsets with divergent and complementary functions. J Exp Med 204, 3037-3047 (2007).

Potteaux S, Gautier E L, Hutchison S B, van Rooijen N, Rader D J, Thomas M J, Sorci-Thomas M G, Randolph G J Suppressed monocyte recruitment drives macrophage removal from atherosclerotic plaques of Apoe−/− mice during disease regression. J Clin Invest 121 (5):2025-2036 (2011). doi: 43802 [pii] 10.1172/JCI43802.

Radsak M P, Salih H R, Rammensee H, Schild H. Triggering receptor expressed on myeloid cells-1 in neutrophil inflammatory responses: differential regulation of activation and survival. J. Immunol; 172:4956-4963 (2004).

Swirski F K, Nahrendorf M, Etzrodt M, Wildgruber M, Cortez-Retamozo V, Panizzi P, Figueiredo J L, Kohler R H, Chudnovskiy A, Waterman P, Aikawa E, Mempel T R, Libby P, Weissleder R, Pittet M J. Identification of splenic reservoir monocytes and their deployment to inflammatory sites. Science 325, 612-616 (2009).

Washington A V, Gibot S, Acevedo I, Gattis J, Quigley L, Feltz R, De La Mota A, Schubert R L, Gomez-Rodriguez J, Cheng J, Dutra A, Pak E, Chertov O, Rivera L, Morales J, Lubkowski J, Hunter R, Schwartzberg P L, McVicar D W. TREM-like transcript-1 protects against inflammation-associated hemorrhage by facilitating platelet aggregation in mice and humans. J Clin Invest. 2009 June; 119(6):1489-501.

The invention claimed is:

1. A method for treating a cardiovascular disease comprising administering a peptide comprising at least 6 consecutive amino acids from the amino acid sequence SEQ ID NO: 3 or SEQ ID NO: 8.

2. The method according to the claim 1, wherein said peptide comprises at least 6 consecutive amino acids from an amino acid sequence selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12.

3. The method according to claim 1 wherein the cardiovascular disease is a myocardial infarction.

4. The method according to claim 1 wherein the cardiovascular disease is atherosclerosis.

5. The method according to the claim 1, wherein said peptide consists of an amino acid sequence selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and SEQ ID NO: 12.

6. The method according to the claim 1, wherein said cardiovascular disease is selected from the group consisting of myocardial and cerebral infarction, acute myocardial infarction, ischemia, coronary heart disease, acute coronary syndrome, stroke, aneurysm, stable or effort angina pectoris, cardiomyopathy, hypertensive heart disease, heart failure (chronic and acute), cor pulmonale, cardiac dysrhythmias, inflammatory heart disease such as endocarditis, myocarditis, peripheral arterial disease, SIRS-associated myocardial and vascular dysfunction and atherosclerosis.

* * * * *

SEQUENCE LISTING

```
<160> NUMBER OF SEQ ID NOS: 13

<210> SEQ ID NO 1
<211> LENGTH: 311
<212> TYPE: PRT
<213> ORGANISM: Homo sapiens

<400> SEQUENCE: 1

Met Gly Leu Thr Leu Leu Leu Leu Leu Gly Leu Glu Gly Gln
1               5                   10                  15

Gly Ile Val Gly Ser Leu Pro Glu Val Leu Gln Ala Pro Val Gly Ser
                20                  25                  30

Ser Ile Leu Val Gln Cys His Tyr Arg Leu Gln Asp Val Lys Ala Gln
            35                  40                      45

Lys Val Trp Cys Arg Phe Leu Pro Glu Gly Cys Gln Pro Leu Val Ser
    50                  55                      60

Ser Ala Val Asp Arg Arg Ala Pro Ala Gly Arg Arg Thr Phe Leu Thr
65                  70                      75                  80

Asp Leu Gly Gly Gly Leu Leu Gln Val Glu Met Val Thr Leu Gln Glu
                    85                  90                  95

Glu Asp Ala Gly Glu Tyr Gly Cys Met Val Asp Gly Ala Arg Gly Pro
                100                 105                 110

Gln Ile Leu His Arg Val Ser Leu Asn Ile Leu Pro Pro Glu Glu Glu
            115                 120                 125

Glu Glu Thr His Lys Ile Gly Ser Leu Ala Glu Asn Ala Phe Ser Asp
    130                 135                 140

Pro Ala Gly Ser Ala Asn Pro Leu Glu Pro Ser Gln Asp Glu Lys Ser
145                 150                 155                 160

Ile Pro Leu Ile Trp Gly Ala Val Leu Leu Val Gly Leu Leu Val Ala
                165                 170                 175

Ala Val Val Leu Phe Ala Val Met Ala Lys Arg Lys Gln Gly Asn Arg
                180                 185                 190

Leu Gly Val Cys Gly Arg Phe Leu Ser Ser Arg Val Ser Gly Met Asn
            195                 200                 205

Pro Ser Ser Val Val His His Val Ser Asp Ser Gly Pro Ala Ala Glu
210                 215                 220

Leu Pro Leu Asp Val Pro His Ile Arg Leu Asp Ser Pro Pro Ser Phe
225                 230                 235                 240

Asp Asn Thr Thr Tyr Thr Ser Leu Pro Leu Asp Ser Pro Ser Gly Lys
                245                 250                 255

Pro Ser Leu Pro Ala Pro Ser Ser Leu Pro Pro Leu Pro Pro Lys Val
            260                 265                 270

Leu Val Cys Ser Lys Pro Val Thr Tyr Ala Thr Val Ile Phe Pro Gly
        275                 280                 285

Gly Asn Lys Gly Gly Gly Thr Ser Cys Gly Pro Ala Gln Asn Pro Pro
    290                 295                 300

Asn Asn Gln Thr Pro Ser Ser
```

```
305                     310

<210> SEQ ID NO 2
<211> LENGTH: 234
<212> TYPE: PRT
<213> ORGANISM: Homo sapiens

<400> SEQUENCE: 2

Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Ser Gly Thr Pro Gly Ser Asn
130                 135                 140

Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
            180                 185                 190

Thr Asn Val Thr Asp Ile Ile Arg Val Pro Val Phe Asn Ile Val Ile
        195                 200                 205

Leu Leu Ala Gly Gly Phe Leu Ser Lys Ser Leu Val Phe Ser Val Leu
    210                 215                 220

Phe Ala Val Thr Leu Arg Ser Phe Val Pro
225                 230

<210> SEQ ID NO 3
<211> LENGTH: 17
<212> TYPE: PRT
<213> ORGANISM: Homo sapiens

<400> SEQUENCE: 3

Leu Gln Glu Glu Asp Ala Gly Glu Tyr Gly Cys Met Val Asp Gly Ala
1               5                   10                  15

Arg

<210> SEQ ID NO 4
<211> LENGTH: 12
<212> TYPE: PRT
<213> ORGANISM: Homo sapiens

<400> SEQUENCE: 4

Leu Gln Glu Glu Asp Ala Gly Glu Tyr Gly Cys Met
1               5                   10
```

```
<210> SEQ ID NO 5
<211> LENGTH: 6
<212> TYPE: PRT
<213> ORGANISM: Homo sapiens

<400> SEQUENCE: 5

Leu Gln Glu Glu Asp Ala
1               5

<210> SEQ ID NO 6
<211> LENGTH: 6
<212> TYPE: PRT
<213> ORGANISM: Homo sapiens

<400> SEQUENCE: 6

Glu Asp Ala Gly Glu Tyr
1               5

<210> SEQ ID NO 7
<211> LENGTH: 6
<212> TYPE: PRT
<213> ORGANISM: Homo sapiens

<400> SEQUENCE: 7

Gly Glu Tyr Gly Cys Met
1               5

<210> SEQ ID NO 8
<211> LENGTH: 17
<212> TYPE: PRT
<213> ORGANISM: Homo sapiens

<400> SEQUENCE: 8

Leu Gln Val Glu Asp Ser Gly Leu Tyr Gln Cys Val Ile Tyr Gln Pro
1               5                   10                  15

Pro

<210> SEQ ID NO 9
<211> LENGTH: 12
<212> TYPE: PRT
<213> ORGANISM: Homo sapiens

<400> SEQUENCE: 9

Leu Gln Val Glu Asp Ser Gly Leu Tyr Gln Cys Val
1               5                   10

<210> SEQ ID NO 10
<211> LENGTH: 6
<212> TYPE: PRT
<213> ORGANISM: Homo sapiens

<400> SEQUENCE: 10

Leu Gln Val Glu Asp Ser
1               5

<210> SEQ ID NO 11
<211> LENGTH: 6
<212> TYPE: PRT
<213> ORGANISM: Homo sapiens

<400> SEQUENCE: 11

Glu Asp Ser Gly Leu Tyr
1               5
```

```
<210> SEQ ID NO 12
<211> LENGTH: 6
<212> TYPE: PRT
<213> ORGANISM: Homo sapiens

<400> SEQUENCE: 12

Gly Leu Tyr Gln Cys Val
1               5

<210> SEQ ID NO 13
<211> LENGTH: 12
<212> TYPE: PRT
<213> ORGANISM: Artificial
<220> FEATURE:
<223> OTHER INFORMATION: synthetic peptide scramble

<400> SEQUENCE: 13

Glu Leu Met Glu Gly Gly Gln Glu Cys Ala Asp Tyr
1               5                   10
```